United States Patent
Himmelspach et al.

(12) 
(10) Patent No.: US 6,573,071 B1
(45) Date of Patent: Jun. 3, 2003

(54) FACTOR X ANALOGUES WITH A MODIFIED PROTEASE CLEAVAGE SITE

(75) Inventors: Michele Himmelspach, Leopoldsdorf (AT); Uwe Schlokat, Orth/Donau (AT); Friedrich Dorner, Vienna (AT); Andreas Fisch, St. Gallen (CH); Johann Eibl, Vienna (AT)

(73) Assignee: Baxter Aktiengesellschaft, Vienna (AT)

(*) Notice: Subject to any disclaimer, the term of this patent is extended or adjusted under 35 U.S.C. 154(b) by 0 days.

(21) Appl. No.: 09/367,791

(22) PCT Filed: Feb. 27, 1998

(86) PCT No.: PCT/AT98/00045

§ 371 (c)(1),
(2), (4) Date: Nov. 12, 1999

(87) PCT Pub. No.: WO98/38317

PCT Pub. Date: Sep. 3, 1998

(30) Foreign Application Priority Data

Feb. 27, 1997 (AT) .................................. 335/97

(51) Int. Cl.[7] .......................... C12P 21/00; C07K 1/00; C07K 14/00; A61K 35/14; A61K 38/48

(52) U.S. Cl. .................... 435/69.6; 435/69.1; 435/69.2; 424/94.64; 514/2; 514/8; 514/12; 514/21; 530/384; 530/395

(58) Field of Search ............................. 435/69.1, 69.2, 435/69.6; 424/94.64; 514/2, 8, 12, 21; 530/384, 395

(56) References Cited

U.S. PATENT DOCUMENTS

| | | | |
|---|---|---|---|
| 4,501,731 A | 2/1985 | Tishkoff et al. | 424/101 |
| 5,460,950 A | 10/1995 | Barr et al. | 435/69.1 |
| 5,858,658 A | 1/1999 | Haemmerle et al. | 435/6 |
| 6,210,929 B1 | 4/2001 | Schlokat et al. | 435/69.7 |

FOREIGN PATENT DOCUMENTS

| | | |
|---|---|---|
| EP | 0 651 054 A1 | 8/1994 |
| EP | 0 714 987 A2 | 9/1995 |
| EP | 0 775 750 A2 | 11/1996 |

OTHER PUBLICATIONS

Wells et al. Additivity of Mutation Effects in Proteins, (1990) Biochemistry 29: 8509–8517.*
Ngo et al. Computational Complexity, Protein Structure Prediction and the Levinthal Paradox in The Protein Folding Problem and Tertiary Structure Prediction, 1994, Merz and Le Grand, editors, Birkhauser, Boston, Chapter 14, p492–495.*
Translation of 1st Preliminary Notice in Austrian Patent Application No. A 335/97–1, stamped received Sep. 29, 1997 by the Austrian Patent Office.
Wolf D.L. et al., "Design of Constructs for the Expression of Biologically Active Recombinant Human Factors X and Xa. Kinetic Analysis of the Expressed Proteins", *J. Biol. Chem.*, vol. 21, 1991, pp. 13726–13730, XP002065182.
Leytus S. et al., "Gene for Human Factor X: A Blood Coagulation Factor Whose Gene Organization is Essentially Identical With That of Factor IX and Protein C", *Biochem.*, vol. 25, 1986, pp. 5098–5102, XP002065183.
International Search Report for PCT/AT98/00045, dated Jun. 3, 1998.
Bajaj, S.P. et al., "Simultaneous Purification of Bovine Prothrombin and Factor X", *J. Biol. Chem.*, vol. 248, 1973, pp. 7729–7741.
Barr, P.J., "Mammalian Subtilisins: The Long–Sought Dibasic Processing Endoproteases", *Cell*, vol. 66, 1991, pp. 1–3.
Sherrill, G.B. et al., "Inactivation of Human Blood Coagulation Factor X by Chemical Modification of Gamma–Carboxyglutamic Acid Residues", *Enzymes*, vol. 102, 102:2489q, 1985, p. 2490.
Morita et al., "Structural and Functional Characteristics of a Proteolytically Modified 'Gla Domain–less' Bovine Factor X and Xa (des light chain residues1–44)." *General Biochem.*, vol. 92, 92:71374k, 1980, p. 71379.
Clackson, T. et al., "PCR A Practical Approach; General Applications of PCR to Gene Cloning and Manipulation", Eds. McPherson, Quirke and Taylor, 1991, pp. 187–214.
Eby, C.S. et al., "Characterization of the Structure and Function of the Carboxy Terminal Peptide of Human Factor X", *Blood*, vol. 80, Supp. 1, 1214, 1992, p. 1215.
Elsinger, F., "Laboratory Tests of Activated Prothrombin Complex Preparations;Activated Prothrombin Complex Concentrates", Eds. Mariani, Russo and Mandelli, 1982, pp. 77–87.
Fair, D.S. and Bahnak, B.R., "Human Hepatoma Cells Secrete Single Chain Factor X, Prothrombin, and Antithrombin III", *Blood*, vol. 64, 1984, pp. 194–204.
Fung, M.R. et al., "Characterization of an Almost Full–Length cDNA Coding for Human Blood Coagulation Factor X", *PNAS*, vol. 82, 1985, pp. 3591–3595.
Official Action of Aug. 26, 1997 Issued With Respect To Austrian Priority Application A 335/97.
Giles, A.R. et al., "A Combination of Factor Xa and Phosphatidylcholine–phosphatidylserine Vesicles Bypasses Factor VIII in vivo", *British J. of Haematology*, 69, 1988, pp. 491–497.

(List continued on next page.)

Primary Examiner—Christopher S. F. Low
Assistant Examiner—Holly Schnizer
(74) Attorney, Agent, or Firm—Townsend and Townsend and Crew, L.L.P.

(57) ABSTRACT

Factor X analogues having a modification in the region of the natural Factor Xa activation cleavage site, said modification representing a processing site of a protease not naturally cleaving in this region of the Factor X sequence, preparations containing the Factor X analogues according to the invention, and processes for the preparation thereof are described.

64 Claims, 13 Drawing Sheets

OTHER PUBLICATIONS

Gordon, V.M. et al., "Proteolytic Activation of Bacterial Toxins by Eukaryotic Cells Is Performed by Furin and by Additional Cellular Proteases", *Infect. Immunol.* vol. 63, 1995, pp. 82–87.

Jetsy, J. et al., "The Mechanism of Activation of Factor X: Kinetic Control of Alternative Pathways Leading to the Formation of Activated Factor X", *J. Biol. Chem.*, vol. 249, 1974, pp. 5614–5622.

Mertens, K. and Bertina, R.M., "Pathways in the Activation of Human Coagulation Factor X", *Biochem. J.*, vol. 185, 1980, pp. 647–658.

Messier, T.L. et al., "Cloning and Expression in COS–1 Cells of a Full–Length cDNA Encoding Human Coagulation Factor X", *Gene*, vol. 90, 1991, pp. 291–294.

Moehring, J.M. and Moehring, T.J., "Strains of CHO–K1 Cells Resistant to Pseudomonas Exotoxin A and Cross–Resistant to Diphtheria Toxin and Viruses", *Infection and Immunity*, vol. 41, 1983, pp. 998–1009.

Ohnishi, Y. et al., "A Furin–Defective Cell Line Is Able to Process Correctly the gp160 of Human Immunodeficiency Virus Type 1", *J. Virol.*, vol. 68, 1994, pp. 4075–4079.

Pryzdial, E.L.G. and Kessler, G.E., "Autoproteolysis or Plasmin–mediated Cleavage of Factor Xaα Exposes a Plasminogen Binding Site and Inhibits Coagulation", *J. Biol. Chem.*, vol. 271, 1996, pp. 16614–16620.

Pryzdial, E.L.G. and Kessler, G.E., "Kinetics of Blood Coagulation Factor Xaα Autoproteolytic Conversion to Factor Xaβ", *J. Biol. Chem.*, vol. 271, 1996, pp. 16621–16626.

Rehemtulla, A. and Kaufman, R.J., "Preferred Sequence Requirements for Cleavage of Pro–von Willebrand Factor by Propeptide–Processing Enzymes", *Blood*, vol. 79, 1992, pp. 2349–2355.

Rudolph, A.E. et al., "Expression, Purification, and Characterization of Recombinant Human Factor $X^1$", *Protein Expression & Purification*, vol. 10, 1997, pp. 373–378.

Teng, C. and Seegers, W.H., "Production of Factor X and Factor Xa Variants With Thrombin, Acutin and by Autolysis", *Thrombosis Res.* vol. 22, 1981, pp. 213–220.

Urlaub, G. and Chasin, L.A., "Isolation of Chinese Hamster Cell Mutants Deficient in Dihydrofolate Reductase Activity", *PNAS*, vol. 77, 1980, pp. 4216–4220.

Wallin, R. et al., "Intracellular Proteolytic Processing of the Two–Chain Vitamin K–Dependent Coagulation Factor X", *Thrombosis Res.* vol. 73, 1994, pp. 395–403.

Watzke, H.H. and High, Katherine A., "Factor X", *Molecular Basis of Thrombosis and Hemostasis*, Eds. High & Roberts, 1995, pp. 239–255.

* cited by examiner (-40)
1
Met Gly Arg Pro Leu His Leu Val Leu Leu Ser Ala Ser Leu Ala Gly Leu Leu Leu
ATG GGG CGC CCA CTG CAC CTC GTC CTG CTC AGT GCC TCC CTG GCT GGC CTC CTG CTG
          9           18          27          36          45          54

(-4)      (-1)
                                                                              40
Leu Gly Glu Ser Leu Phe Ile Arg Arg Glu Gln Ala Asn Asn Ile Leu Ala Arg Val Thr Arg
CTC GGG GAA AGT CTG TTC ATC CGC AGG GAG CAG GCC AAC AAC ATC CTG GCG AGG GTC ACG AGG
         66          75          84          93         102         111         120

(+1)
41
Ala Asn Ser Phe Leu Glu Glu Met Lys Lys Gly His Leu Glu Arg Glu Cys Met Glu Glu Thr
GCC AAT TCC TTT CTT GAA GAG ATG AAG AAA GGA CAC CTC GAA AGA GAG TGC ATG GAA GAG ACC
        129         138         147         156         165         174         183

Cys Ser Tyr Glu Glu Ala Arg Glu Val Phe Glu Asp Ser Asp Lys Thr Asn Glu Phe Trp Asn
TGC TCA TAC GAA GAG GCC CGC GAG GTC TTT GAG GAC AGC GAC AAG ACG AAT GAA TTC TGG AAT
        192         201         210         219         228         237         246

Lys Tyr Lys Asp Gly Asp Gln Cys Glu Thr Ser Pro Cys Gln Asn Gln Gly Lys Cys Lys Asp
AAA TAC AAA GAT GGC GAC CAG TGT GAG ACC AGT CCT TGC CAG AAC CAG GGC AAA TGT AAA GAC
        255         264         273         282         291         300         309

Gly Leu Gly Glu Tyr Thr Cys Thr Cys Leu Glu Gly Phe Glu Gly Lys Asn Cys Glu Leu Phe
GGC CTC GGG GAA TAC ACC TGC ACC TGT TTA GAA GGA TTC GAA GGC AAA AAC TGT GAA TTA TTC
        318         327         336         345         354         363         372

Thr Arg Lys Leu Cys Ser Leu Asp Asn Gly Asp Cys Asp Gln Phe Cys His Glu Glu Gln Asn
ACA CGG AAG CTC TGC AGC CTG GAC AAC GGG GAC TGT GAC CAG TTC TGC CAC GAG GAA CAG AAC
        381         390         399         408         417         426         435

Ser Val Val Cys Ser Cys Ala Arg Gly Tyr Thr Leu Ala Asp Asn Gly Lys Ala Cys Ile Pro
TCT GTG GTG TGC TCC TGC GCC CGC GGG TAC ACC CTG GCT GAC AAC GGC AAG GCC TGC ATT CCC
        444         453         462         471         480         489         498

178 179 180 181 182 183
Thr Gly Pro Tyr Pro Cys Gly Lys Gln Thr Leu Glu Arg Arg Lys Arg Ser Val Ala Gln Ala
ACA GGG CCC TAC CCC TGT GGG AAA CAG ACC CTG GAA CGC AGG AAG AGG TCA GTG GCC CAG GCC
        507         516         525         534         543         552         561

Thr Ser Ser Ser Gly Glu Ala Pro Asp Ser Ile Thr Trp Lys Pro Tyr Asp Ala Ala Asp Leu
ACC AGC AGC AGC GGG GAG GCC CCT GAC AGC ATC ACA TGG AAG CCA TAT GAT GCA GCC GAC CTG
        570         579         588         597         606         615         624

R6
                                                                              229
Asp Pro Thr Glu Asn Pro Phe Asp Leu Leu Asp Phe Asn Gln Thr Gln Pro Glu Arg Gly Asp
GAC CCC ACC GAG AAC CCC TTC GAC CTG CTT GAC TTC AAC CAG ACG CAG CCT GAG AGG GGC GAC
        633         642         651         660         669         678         687

Fig.1A

```
R5  R4  R3  R2      R1
            234 235
Asn Asn Leu Thr Arg Ile Val Gly Gly Gln Glu Cys Lys Asp Gly Glu Cys Pro Trp Gln Ala
AAC AAC CTC ACC AGG ATC GTG GGA GGC CAG GAA TGC AAG GAC GGG GAG TGT CCC TGG CAG GCC
            696         705         714         723         732         741         750

Leu Leu Ile Asn Glu Glu Asn Glu Gly Phe Cys Gly Gly Thr Ile Leu Ser Glu Phe Tyr Ile
CTG CTC ATC AAT GAG GAA AAC GAG GGT TTC TGT GGT GGA ACT ATT CTG AGC GAG TTC TAC ATC
            759         768         777         786         795         804         813

Leu Thr Ala Ala His Cys Leu Tyr Gln Ala Lys Arg Phe Lys Val Arg Val Gly Asp Arg Asn
CTA ACG GCA GCC CAC TGT CTC TAC CAA GCC AAG AGA TTC AAG GTG AGG GTA GGG GAC CGG AAC
            822         831         840         849         858         867         876

Thr Glu Gln Glu Glu Gly Gly Glu Ala Val His Glu Val Glu Val Val Ile Lys His Asn Arg
ACG GAG CAG GAG GAG GGC GGT GAG GCG GTG CAC GAG GTG GAG GTG GTC ATC AAG CAC AAC CGG
            885         894         903         912         921         930         939

Phe Thr Lys Glu Thr Tyr Asp Phe Asp Ile Ala Val Leu Arg Leu Lys Thr Pro Ile Thr Phe
TTC ACA AAG GAG ACC TAT GAC TTC GAC ATC GCC GTG CTC CGG CTC AAG ACC CCC ATC ACC TTC
            948         957         966         975         984         993         1002

Arg Met Asn Val Ala Pro Ala Cys Leu Pro Glu Arg Asp Trp Ala Glu Ser Thr Leu Met Thr
CGC ATG AAC GTG GCG CCT GCC TGC CTC CCC GAG CGT GAC TGG GCC GAG TCC ACG CTG ATG ACG
            1011        1020        1029        1038        1047        1056        1065

Gln Lys Thr Gly Ile Val Ser Gly Phe Gly Arg Thr His Glu Lys Gly Arg Gln Ser Thr Arg
CAG AAG ACG GGG ATT GTG AGC GGC TTC GGG CGC ACC CAC GAG AAG GGC CGG CAG TCC ACC AGG
            1074        1083        1092        1101        1110        1119        1128

Leu Lys Met Leu Glu Val Pro Tyr Val Asp Arg Asn Ser Cys Lys Leu Ser Ser Ser Phe Ile
CTC AAG ATG CTG GAG GTG CCC TAC GTG GAC CGC AAC AGC TGC AAG CTG TCC AGC AGC TTC ATC
            1137        1146        1155        1164        1173        1182        1191

Ile Thr Gln Asn Met Phe Cys Ala Gly Tyr Asp Thr Lys Gln Glu Asp Ala Cys Gln Gly Asp
ATC ACC CAG AAC ATG TTC TGT GCC GGC TAC GAC ACC AAG CAG GAG GAT GCC TGC CAG GGG GAC
            1200        1209        1218        1227        1236        1245        1254

Ser Gly Gly Pro His Val Thr Arg Phe Lys Asp Thr Tyr Phe Val Thr Gly Ile Val Ser Trp
AGC GGG GGC CCG CAC GTC ACC CGC TTC AAG GAC ACC TAC TTC GTG ACA GGC ATC GTC AGC TGG
            1263        1272        1281        1290        1399        1308        1317

Gly Glu Ser Cys Ala Arg Lys Gly Lys Tyr Gly Ile Tyr Thr Lys Val Thr Ala Phe Leu Lys
GGA GAG AGC TGT GCC CGT AAG GGG AAG TAC GGG ATC TAC ACC AAG GTC ACC GCC TTC CTC AAG
            1326        1335        1344        1353        1362        1371        1380

469 470             475 476             480
Trp Ile Asp Arg Ser Met Lys Thr Arg Gly Leu Pro Lys Ala Lys Ser His Ala Pro Glu Val
TGG ATC GAC AGG TCC ATG AAA ACC AGG GGC TTG CCC AAG GCC AAG AGC CAT GCC CCG GAG GTC
            1389        1398        1407        1416        1425        1434        1443

488
Ile Thr Ser Ser Pro Leu Lys TER
ATA ACG TCC TCT CCA TTA AAG TGA
            1452        1461        1467

PRE-PEPTIDE
"CONNECTING" TRIPEPTIDE
ACTIVATION PEPTIDE
```

Fig.1B

Fig. 5
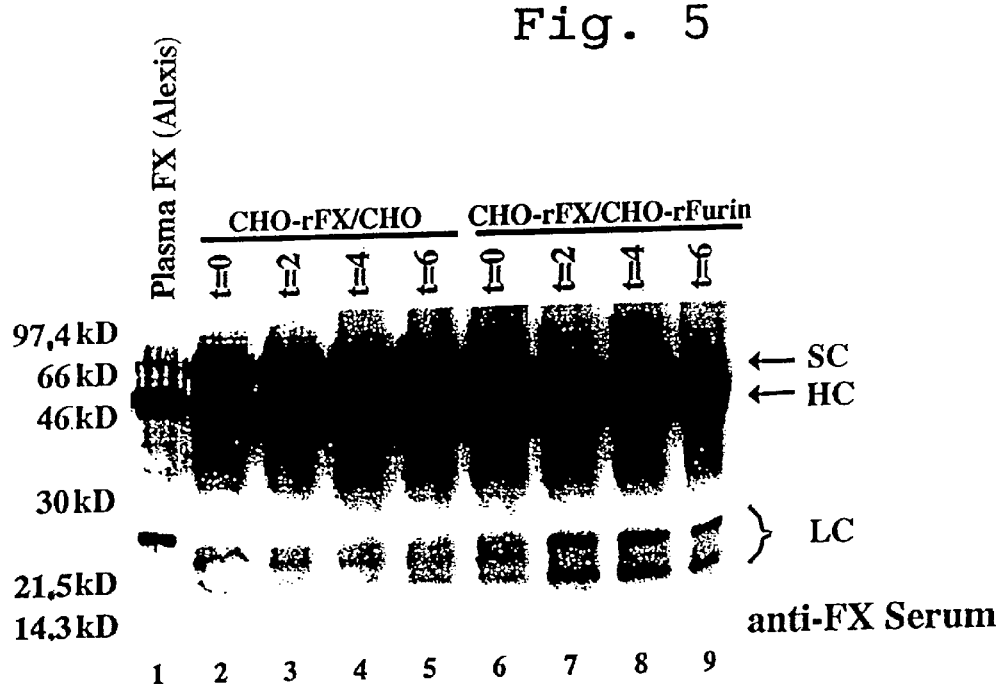
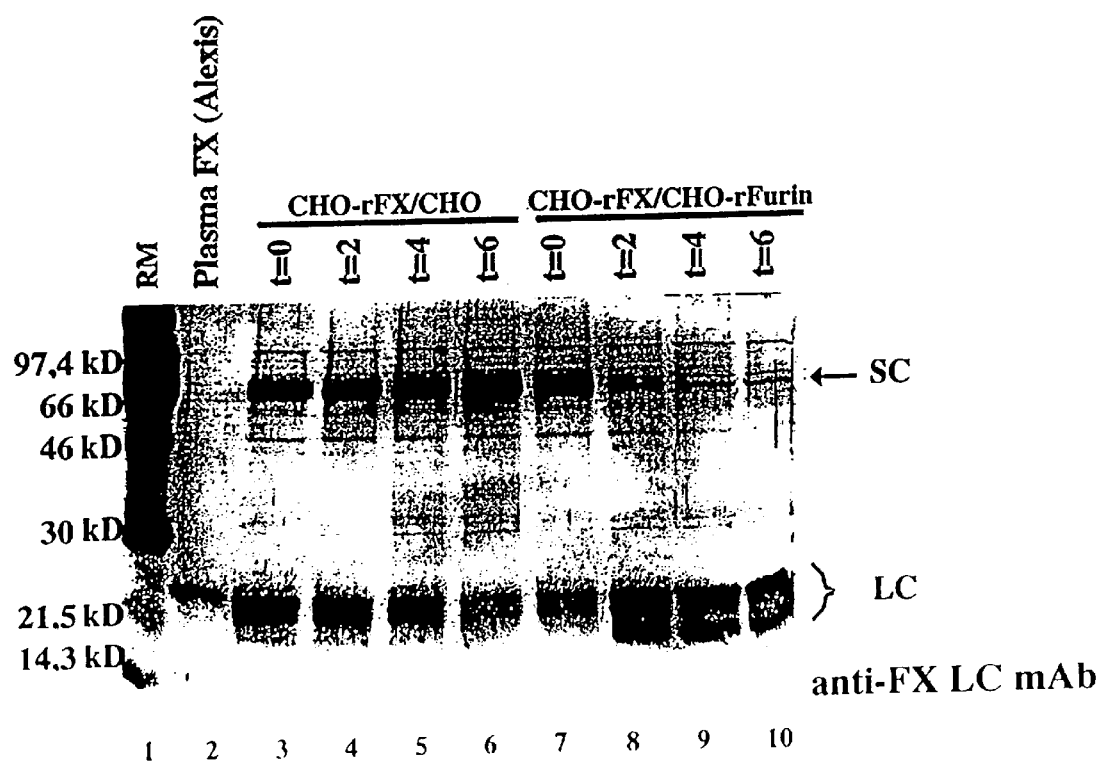
t=period of incubation at 37°C (hours)

SEQUENCE LISTING

```
(1) GENERAL INFORMATION:

(iii) NUMBER OF SEQUENCES: 122

(2) INFORMATION FOR SEQ ID NO: 1:

(i) SEQUENCE CHARACTERISTICS:
          (A) LENGTH: 34 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 1:

ATTACTCGAG AAGCTTACCA TGGGGCGCCC ACTG                              34

(2) INFORMATION FOR SEQ ID NO: 2:
```

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

ATTACAATTG CTGCAGGGAT CCAC                                                  24

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

CCCACAGGGC CCTACCCCTG T                                                     21

(2) INFORMATION FOR SEQ ID NO: 4:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

ACCAGTTAAC CCTGGTGAAG TCGTTGTCGC CCCTCTC                                    37

(2) INFORMATION FOR SEQ ID NO: 5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

ACCATCGCGA CCTGGTCAGG TTGTTGTC                                              28

(2) INFORMATION FOR SEQ ID NO: 6:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

ACCAGAATCG ATTCTGGGTT TGATGTTGTC GCCCCTCTC                                  39

(2) INFORMATION FOR SEQ ID NO: 7:

(i) SEQUENCE CHARACTERISTICS:
        (A) LENGTH: 39 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO: 7:

ACCAGAATCG ATTCTGGTCA TGCTGTTGTC GCCCCTCTC                       39

(2) INFORMATION FOR SEQ ID NO: 8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

ACCAGAATCG ATTCTTCCTT GGGGGTTGTC GCCCCTCTC                       39

(2) INFORMATION FOR SEQ ID NO: 9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

ACCAGAATCG ATTCTCGTTT TCATGTTGTC GCCCCTCTC                       39

(2) INFORMATION FOR SEQ ID NO: 10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

ACCAGAATCG ATTCTTCCCT CGATGTTGTC GCCCCTCTC                       39

(2) INFORMATION FOR SEQ ID NO: 11:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

ACCAGAATCG ATTCTTTTCC TCCTGTTGTC GCCCCTCTC                       39

(2) INFORMATION FOR SEQ ID NO: 12:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

ACCAGAATCG ATTCTCCTCA CCCTGTTGTC GCCCCTCTC          39

(2) INFORMATION FOR SEQ ID NO: 13:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

ACCAGAATCG ATTCTCCTCC TCCTGTTGTC GCCCCTCTC          39

(2) INFORMATION FOR SEQ ID NO: 14:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

ACCAGAATCG ATTCTTTTGG GCCTGTTGTC GCCCCTCTC          39

(2) INFORMATION FOR SEQ ID NO: 15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

ACCAGAATCG ATTCTTTTCC TGATGTTGTC GCCCCTCTC          39

(2) INFORMATION FOR SEQ ID NO: 16:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

ACCAGAATCG ATTCTTTTGC TCCTGTTGTC GCCCCTCTC          39

(2) INFORMATION FOR SEQ ID NO: 17:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

ACCAGAATCG ATTCTGGTCA CCCTGTTGTC GCCCCTCTC          39

(2) INFORMATION FOR SEQ ID NO: 18:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

ACCAGAATCG ATTCTTTTGA GCCTGTTGTC GCCCCTCTC                      39

(2) INFORMATION FOR SEQ ID NO: 19:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

ACCAGAATCG ATTCTCGTGC TCGTGTTGTC GCCCCTCTC                      39

(2) INFORMATION FOR SEQ ID NO: 20:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

GTCACCGCCT TCCTCAAGTG GATCGACAGG TCCATGAAAA CCAGGTGAA              49

(2) INFORMATION FOR SEQ ID NO: 21:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

CTAGTTCACC TGGTTTTCAT GGACCTGTCG ATCCACTTGA GGAAGGCG               48

(2) INFORMATION FOR SEQ ID NO: 22:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

GTCACCGCCT TCCTCAAGTG GATCGACAGG TCCATGAAAA CCAAGGGCTT GCCCAAG        57

(2) INFORMATION FOR SEQ ID NO: 23:

(i) SEQUENCE CHARACTERISTICS:
    (A) LENGTH: 57 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 23:

TTGGCCTTGG GCAAGCCCTT GGTTTTCATG GACCTGTCGA TCCACTTGAG GAAGGCG         57

(2) INFORMATION FOR SEQ ID NO: 24:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

GCCAAGAGCC ATGCCCCGGA GGTCATAACG TCCTCTCCAT TAAAGTGAGA TCCCA           55

(2) INFORMATION FOR SEQ ID NO: 25:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

CTAGTGGGAT CTCACTTTAA TGGAGAGGAC GTTATGACCT CCGGGGCATG GCTC            54

(2) INFORMATION FOR SEQ ID NO: 26:

(i) SEQUENCE CHARACTERISTICS:
        (A) LENGTH: 1467 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1...1467
        (D) OTHER INFORMATION: Factor X (xi) SEQUENCE DESCRIPTION: SEQ ID NO: 26:

```
ATG GGG CGC CCA CTG CAC CTC GTC CTG CTC AGT GCC TCC CTG GCT GGC        48
Met Gly Arg Pro Leu His Leu Val Leu Leu Ser Ala Ser Leu Ala Gly
 1               5                  10                  15

CTC CTG CTG CTC GGG GAA AGT CTG TTC ATC CGC AGG GAG CAG GCC AAC        96
Leu Leu Leu Leu Gly Glu Ser Leu Phe Ile Arg Arg Glu Gln Ala Asn
                20                  25                  30

AAC ATC CTG GCG AGG GTC ACG AGG GCC AAT TCC TTT CTT GAA GAG ATG       144
Asn Ile Leu Ala Arg Val Thr Arg Ala Asn Ser Phe Leu Glu Glu Met
            35                  40                  45

AAG AAA GGA CAC CTC GAA AGA GAG TGC ATG GAA GAG ACC TGC TCA TAC       192
Lys Lys Gly His Leu Glu Arg Glu Cys Met Glu Glu Thr Cys Ser Tyr
        50                  55                  60

GAA GAG GCC CGC GAG GTC TTT GAG GAC AGC GAC AAG ACG AAT GAA TTC       240
Glu Glu Ala Arg Glu Val Phe Glu Asp Ser Asp Lys Thr Asn Glu Phe
65                  70                  75                  80
```

-continued

| | |
|---|---|
| TGG AAT AAA TAC AAA GAT GGC GAC CAG TGT GAG ACC AGT CCT TGC CAG<br>Trp Asn Lys Tyr Lys Asp Gly Asp Gln Cys Glu Thr Ser Pro Cys Gln<br>              85                     90                 95 | 288 |
| AAC CAG GGC AAA TGT AAA GAC GGC CTC GGG GAA TAC ACC TGC ACC TGT<br>Asn Gln Gly Lys Cys Lys Asp Gly Leu Gly Glu Tyr Thr Cys Thr Cys<br>           100                  105               110 | 336 |
| TTA GAA GGA TTC GAA GGC AAA AAC TGT GAA TTA TTC ACA CGG AAG CTC<br>Leu Glu Gly Phe Glu Gly Lys Asn Cys Glu Leu Phe Thr Arg Lys Leu<br>         115                 120               125 | 384 |
| TGC AGC CTG GAC AAC GGG GAC TGT GAC CAG TTC TGC CAC GAG GAA CAG<br>Cys Ser Leu Asp Asn Gly Asp Cys Asp Gln Phe Cys His Glu Glu Gln<br>130                 135               140 | 432 |
| AAC TCT GTG GTG TGC TCC TGC GCC CGC GGG TAC ACC CTG GCT GAC AAC<br>Asn Ser Val Val Cys Ser Cys Ala Arg Gly Tyr Thr Leu Ala Asp Asn<br>145                 150               155               160 | 480 |
| GGC AAG GCC TGC ATT CCC ACA GGG CCC TAC CCC TGT GGG AAA CAG ACC<br>Gly Lys Ala Cys Ile Pro Thr Gly Pro Tyr Pro Cys Gly Lys Gln Thr<br>                 165               170               175 | 528 |
| CTG GAA CGC AGG AAG AGG TCA GTG GCC CAG GCC ACC AGC AGC AGC GGG<br>Leu Glu Arg Arg Lys Arg Ser Val Ala Gln Ala Thr Ser Ser Ser Gly<br>         180                 185               190 | 576 |
| GAG GCC CCT GAC AGC ATC ACA TGG AAG CCA TAT GAT GCA GCC GAC CTG<br>Glu Ala Pro Asp Ser Ile Thr Trp Lys Pro Tyr Asp Ala Ala Asp Leu<br>195                 200               205 | 624 |
| GAC CCC ACC GAG AAC CCC TTC GAC CTG CTT GAC TTC AAC CAG ACG CAG<br>Asp Pro Thr Glu Asn Pro Phe Asp Leu Leu Asp Phe Asn Gln Thr Gln<br>         210                215               220 | 672 |
| CCT GAG AGG GGC GAC AAC AAC CTC ACC AGG ATC GTG GGA GGC CAG GAA<br>Pro Glu Arg Gly Asp Asn Asn Leu Thr Arg Ile Val Gly Gly Gln Glu<br>225                 230               235               240 | 720 |
| TGC AAG GAC GGG GAG TGT CCC TGG CAG GCC CTG CTC ATC AAT GAG GAA<br>Cys Lys Asp Gly Glu Cys Pro Trp Gln Ala Leu Leu Ile Asn Glu Glu<br>                 245               250               255 | 768 |
| AAC GAG GGT TTC TGT GGT GGA ACT ATT CTG AGC GAG TTC TAC ATC CTA<br>Asn Glu Gly Phe Cys Gly Gly Thr Ile Leu Ser Glu Phe Tyr Ile Leu<br>         260                 265               270 | 816 |
| ACG GCA GCC CAC TGT CTC TAC CAA GCC AAG AGA TTC AAG GTG AGG GTA<br>Thr Ala Ala His Cys Leu Tyr Gln Ala Lys Arg Phe Lys Val Arg Val<br>275                 280               285 | 864 |
| GGG GAC CGG AAC ACG GAG CAG GAG GAG GGC GGT GAG GCG GTG CAC GAG<br>Gly Asp Arg Asn Thr Glu Gln Glu Glu Gly Gly Glu Ala Val His Glu<br>         290                295               300 | 912 |
| GTG GAG GTG GTC ATC AAG CAC AAC CGG TTC ACA AAG GAG ACC TAT GAC<br>Val Glu Val Val Ile Lys His Asn Arg Phe Thr Lys Glu Thr Tyr Asp<br>305                 310               315               320 | 960 |
| TTC GAC ATC GCC GTG CTC CGG CTC AAG ACC CCC ATC ACC TTC CGC ATG<br>Phe Asp Ile Ala Val Leu Arg Leu Lys Thr Pro Ile Thr Phe Arg Met<br>                 325               330               335 | 1008 |
| AAC GTG GCG CCT GCC TGC CTC CCC GAG CGT GAC TGG GCC GAG TCC ACG<br>Asn Val Ala Pro Ala Cys Leu Pro Glu Arg Asp Trp Ala Glu Ser Thr<br>                 340               345               350 | 1056 |
| CTG ATG ACG CAG AAG ACG GGG ATT GTG AGC GGC TTC GGG CGC ACC CAC<br>Leu Met Thr Gln Lys Thr Gly Ile Val Ser Gly Phe Gly Arg Thr His<br>         355                 360               365 | 1104 |
| GAG AAG GGC CGG CAG TCC ACC AGG CTC AAG ATG CTG GAG GTG CCC TAC<br>Glu Lys Gly Arg Gln Ser Thr Arg Leu Lys Met Leu Glu Val Pro Tyr<br>370                 375               380 | 1152 |
| GTG GAC CGC AAC AGC TGC AAG CTG TCC AGC AGC TTC ATC ATC ACC CAG<br>Val Asp Arg Asn Ser Cys Lys Leu Ser Ser Ser Phe Ile Ile Thr Gln | 1200 |

```
                385                 390                 395                 400
AAC ATG TTC TGT GCC GGC TAC GAC ACC AAG CAG GAG GAT GCC TGC CAG              1248
Asn Met Phe Cys Ala Gly Tyr Asp Thr Lys Gln Glu Asp Ala Cys Gln
                        405                 410                 415

GGG GAC AGC GGG GGC CCG CAC GTC ACC CGC TTC AAG GAC ACC TAC TTC              1296
Gly Asp Ser Gly Gly Pro His Val Thr Arg Phe Lys Asp Thr Tyr Phe
                420                 425                 430

GTG ACA GGC ATC GTC AGC TGG GGA GAG AGC TGT GCC CGT AAG GGG AAG              1344
Val Thr Gly Ile Val Ser Trp Gly Glu Ser Cys Ala Arg Lys Gly Lys
            435                 440                 445

TAC GGG ATC TAC ACC AAG GTC ACC GCC TTC CTC AAG TGG ATC GAC AGG              1392
Tyr Gly Ile Tyr Thr Lys Val Thr Ala Phe Leu Lys Trp Ile Asp Arg
        450                 455                 460

TCC ATG AAA ACC AGG GGC TTG CCC AAG GCC AAG AGC CAT GCC CCG GAG              1440
Ser Met Lys Thr Arg Gly Leu Pro Lys Ala Lys Ser His Ala Pro Glu
465                 470                 475                 480

GTC ATA ACG TCC TCT CCA TTA AAG TGA                                          1467
Val Ile Thr Ser Ser Pro Leu Lys
                485
```

(2) INFORMATION FOR SEQ ID NO: 27:

(i) SEQUENCE CHARACTERISTICS:
        (A) LENGTH: 488 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 27:

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
```

```
                        210                 215                 220
Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
                260                 265                 270

Thr Ala Ala His Cys Leu Tyr Gln Ala Lys Arg Phe Lys Val Arg Val
                275                 280                 285

Gly Asp Arg Asn Thr Glu Gln Glu Glu Gly Gly Glu Ala Val His Glu
290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
                340                 345                 350

Leu Met Thr Gln Lys Thr Gly Ile Val Ser Gly Phe Gly Arg Thr His
                355                 360                 365

Glu Lys Gly Arg Gln Ser Thr Arg Leu Lys Met Leu Glu Val Pro Tyr
370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
                420                 425                 430

Val Thr Gly Ile Val Ser Trp Gly Glu Ser Cys Ala Arg Lys Gly Lys
                435                 440                 445

Tyr Gly Ile Tyr Thr Lys Val Thr Ala Phe Leu Lys Trp Ile Asp Arg
                450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

(2) INFORMATION FOR SEQ ID NO: 28:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 2...2
        (D) OTHER INFORMATION: Xaa = Asp, Phe, Thr, Arg, Leu or Ser (xi) SEQUENCE DESCRIPTION: SEQ ID NO: 28:

Gly Xaa Xaa Xaa Xaa Xaa Arg Xaa
 1               5

(2) INFORMATION FOR SEQ ID NO: 29:

(i) SEQUENCE CHARACTERISTICS:
        (A) LENGTH: 8 amino acids
```

(B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 29:

Gly Phe Asn Asp Phe Thr Arg Val
1               5

(2) INFORMATION FOR SEQ ID NO: 30:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 30:

Gly Asp Asn Asp Phe Thr Arg Val
1               5

(2) INFORMATION FOR SEQ ID NO: 31:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 31:

Gly Asp Asn Asn Leu Thr Arg Ser
1               5

(2) INFORMATION FOR SEQ ID NO: 32:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 32:

Gly Thr Lys Ile Lys Pro Arg Ile
1               5

(2) INFORMATION FOR SEQ ID NO: 33:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 33:

Gly Thr Asn Ile Lys Pro Arg Ile
1               5

(2) INFORMATION FOR SEQ ID NO: 34:

(i) SEQUENCE CHARACTERISTICS:

(A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 34:

Gly Asp Lys Ile Lys Pro Arg Ile
1               5

(2) INFORMATION FOR SEQ ID NO: 35:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 35:

Gly Asp Asn Ile Lys Pro Arg Ile
1               5

(2) INFORMATION FOR SEQ ID NO: 36:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 36:

Gly Thr Lys Thr Ser Thr Arg Ile
1               5

(2) INFORMATION FOR SEQ ID NO: 37:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 37:

Gly Thr Asn Thr Ser Thr Arg Ile
1               5

(2) INFORMATION FOR SEQ ID NO: 38:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 38:

Gly Asp Lys Thr Ser Thr Arg Ile
1               5

(2) INFORMATION FOR SEQ ID NO: 39:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

Gly Asp Asn Thr Ser Thr Arg Ile
1               5

(2) INFORMATION FOR SEQ ID NO: 40:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

Gly Leu Ser Ser Met Thr Arg Ile
1               5

(2) INFORMATION FOR SEQ ID NO: 41:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 41:

Gly Leu Asn Ser Met Thr Arg Ile
1               5

(2) INFORMATION FOR SEQ ID NO: 42:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 42:

Gly Asp Ser Ser Met Thr Arg Ile
1               5

(2) INFORMATION FOR SEQ ID NO: 43:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 43:

Gly Asp Asn Ser Met Thr Arg Ile
1               5

(2) INFORMATION FOR SEQ ID NO: 44:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 44:

Gly Ser Lys Pro Gln Gly Arg Ile
1               5

(2) INFORMATION FOR SEQ ID NO: 45:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 45:

Gly Ser Asn Pro Gln Gly Arg Ile
1               5

(2) INFORMATION FOR SEQ ID NO: 46:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 46:

Gly Asp Lys Pro Gln Gly Arg Ile
1               5

(2) INFORMATION FOR SEQ ID NO: 47:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 47:

Gly Asp Asn Pro Gln Gly Arg Ile
1               5

(2) INFORMATION FOR SEQ ID NO: 48:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 48:

Gly Asp Asn Met Lys Thr Arg Ile
1               5

(2) INFORMATION FOR SEQ ID NO: 49:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 49:

Gly Asp Asn Ile Glu Gly Arg Ile
 1               5

(2) INFORMATION FOR SEQ ID NO: 50:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 50:

Gly Leu Glu Arg Arg Lys Arg Ile
 1               5

(2) INFORMATION FOR SEQ ID NO: 51:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 51:

Gly Leu Asn Arg Arg Lys Arg Ile
 1               5

(2) INFORMATION FOR SEQ ID NO: 52:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 52:

Gly Asp Glu Arg Arg Lys Arg Ile
 1               5

(2) INFORMATION FOR SEQ ID NO: 53:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 53:

Gly Asp Asn Arg Arg Lys Arg Ile
 1               5

(2) INFORMATION FOR SEQ ID NO: 54:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 54:

Gly Leu Ala Arg Val Thr Arg Ile
1            5

(2) INFORMATION FOR SEQ ID NO: 55:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 55:

Gly Leu Asn Arg Val Thr Arg Ile
1            5

(2) INFORMATION FOR SEQ ID NO: 56:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 56:

Gly Asp Ala Arg Val Thr Arg Ile
1            5

(2) INFORMATION FOR SEQ ID NO: 57:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 57:

Gly Asp Asn Arg Val Thr Arg Ile
1            5

(2) INFORMATION FOR SEQ ID NO: 58:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 58:

Gly Leu Gln Arg Val Arg Arg Ile
1            5

(2) INFORMATION FOR SEQ ID NO: 59:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 59:

Gly Leu Asn Arg Val Arg Arg Ile
1           5

(2) INFORMATION FOR SEQ ID NO: 60:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 60:

Gly Asp Gln Arg Val Arg Arg Ile
1           5

(2) INFORMATION FOR SEQ ID NO: 61:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 61:

Gly Asp Asn Arg Val Arg Arg Ile
1           5

(2) INFORMATION FOR SEQ ID NO: 62:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 62:

Gly Leu His Arg Arg Arg Arg Ile
1           5

(2) INFORMATION FOR SEQ ID NO: 63:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 63:

Gly Leu Asn Arg Arg Arg Arg Ile

```
1               5
```

(2) INFORMATION FOR SEQ ID NO: 64:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 64:

```
Gly Asp His Arg Arg Arg Arg Ile
1               5
```

(2) INFORMATION FOR SEQ ID NO: 65:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 65:

```
Gly Asp Asn Arg Arg Arg Arg Ile
1               5
```

(2) INFORMATION FOR SEQ ID NO: 66:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 66:

```
Gly Leu Asn Arg Pro Lys Arg Ile
1               5
```

(2) INFORMATION FOR SEQ ID NO: 67:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 67:

```
Gly Asp Asn Arg Pro Lys Arg Ile
1               5
```

(2) INFORMATION FOR SEQ ID NO: 68:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 68:

Gly Leu Arg Ile Arg Lys Arg Ile
1               5

(2) INFORMATION FOR SEQ ID NO: 69:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 69:

Gly Leu Asn Ile Arg Lys Arg Ile
1               5

(2) INFORMATION FOR SEQ ID NO: 70:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 70:

Gly Asp Arg Ile Arg Lys Arg Ile
1               5

(2) INFORMATION FOR SEQ ID NO: 71:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 71:

Gly Asp Asn Ile Arg Lys Arg Ile
1               5

(2) INFORMATION FOR SEQ ID NO: 72:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 72:

Gly Asp Asn Arg Ser Lys Arg Ile
1               5

(2) INFORMATION FOR SEQ ID NO: 73:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 73:

```
Gly Asp Asn Arg Val Thr Arg Ile
1               5
```

(2) INFORMATION FOR SEQ ID NO: 74:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 74:

```
Gly Asp Asn Arg Leu Lys Arg Ile
1               5
```

(2) INFORMATION FOR SEQ ID NO: 75:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 75:

```
Arg Arg Lys Arg Ile
1               5
```

(2) INFORMATION FOR SEQ ID NO: 76:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 76:

```
Asp Phe Thr Arg Val
1               5
```

(2) INFORMATION FOR SEQ ID NO: 77:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 77:

```
Thr Leu Glu Arg Arg Lys Arg Ser Val Ala
1               5                   10
```

(2) INFORMATION FOR SEQ ID NO: 78:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 78:

Asn Leu Thr Arg Ile Val Gly Gly
1               5

(2) INFORMATION FOR SEQ ID NO: 79:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 79:

Asp Phe Thr Arg Val Val Gly Gly
1               5

(2) INFORMATION FOR SEQ ID NO: 80:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 80:

Asn Leu Thr Arg Ser Val Gly Gly
1               5

(2) INFORMATION FOR SEQ ID NO: 81:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 81:

Ile Lys Pro Arg Ile Val Gly Gly
1               5

(2) INFORMATION FOR SEQ ID NO: 82:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 82:

Ser Met Thr Arg Ile Val Gly Gly
1               5

(2) INFORMATION FOR SEQ ID NO: 83:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 83:

Met Lys Thr Arg Ile Val Gly Gly
 1               5

(2) INFORMATION FOR SEQ ID NO: 84:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 84:

Ile Glu Gly Arg Ile Val Gly Gly
 1               5

(2) INFORMATION FOR SEQ ID NO: 85:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 85:

Arg Arg Lys Arg Ile Val Gly Gly
 1               5

(2) INFORMATION FOR SEQ ID NO: 86:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 86:

Arg Val Arg Arg Ile Val Gly Gly
 1               5

(2) INFORMATION FOR SEQ ID NO: 87:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 87:

Arg Arg Arg Arg Ile Val Gly Gly
 1               5

(2) INFORMATION FOR SEQ ID NO: 88:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 88:

Arg Pro Lys Arg Ile Val Gly Gly
  1               5

(2) INFORMATION FOR SEQ ID NO: 89:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 89:

Ile Arg Lys Arg Ile Val Gly Gly
  1               5

(2) INFORMATION FOR SEQ ID NO: 90:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 90:

Arg Ser Lys Arg Ile Val Gly Gly
  1               5

(2) INFORMATION FOR SEQ ID NO: 91:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 91:

Arg Val Thr Arg Ile Val Gly Gly
  1               5

(2) INFORMATION FOR SEQ ID NO: 92:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 92:

Arg Lys Leu Arg Ile Val Gly Gly
  1               5

(2) INFORMATION FOR SEQ ID NO: 93:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 93:

Thr Leu Glu Arg Arg Lys Arg Ser
1               5

(2) INFORMATION FOR SEQ ID NO: 94:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 94:

Pro Gln Gly Arg Ile Val Gly Gly
1               5

(2) INFORMATION FOR SEQ ID NO: 95:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 95:

Thr Ser Thr Arg Ile Val Gly Gly
1               5

(2) INFORMATION FOR SEQ ID NO: 96:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 96:

Xaa Xaa Xaa Arg Xaa Val Gly Gly
1               5

(2) INFORMATION FOR SEQ ID NO: 97:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 97:

Met Lys Thr Arg
1

(2) INFORMATION FOR SEQ ID NO: 98:

(i) SEQUENCE CHARACTERISTICS:
        (A) LENGTH: 5 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO: 98:

Met Lys Thr Lys Gly
1               5

(2) INFORMATION FOR SEQ ID NO: 99:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 99:

Gly Glu Ser Leu Phe Ile Arg Arg Glu Gln
1               5                   10

(2) INFORMATION FOR SEQ ID NO: 100:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 100:

Ile Leu Ala Arg Val Thr Arg Ala Asn Ser Phe Leu Glu Glu
1               5                   10

(2) INFORMATION FOR SEQ ID NO: 101:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 101:

Ser Val Ala Gln Ala Thr Ser
1               5

(2) INFORMATION FOR SEQ ID NO: 102:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 102:

Leu Phe Ile Arg Arg Glu Gln
1               5

(2) INFORMATION FOR SEQ ID NO: 103:

(i) SEQUENCE CHARACTERISTICS:
            (A) LENGTH: 7 amino acids
            (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO: 103:

Ala Asn Ser Phe Leu Glu Glu
 1               5

(2) INFORMATION FOR SEQ ID NO: 104:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 104:

Val Thr Arg Ala Asn Ser Phe Leu Glu Glu
 1               5                  10

(2) INFORMATION FOR SEQ ID NO: 105:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 105:

Arg Val Thr Arg Ala
 1               5

(2) INFORMATION FOR SEQ ID NO: 106:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 106:

Arg Arg Lys Arg Ser
 1               5

(2) INFORMATION FOR SEQ ID NO: 107:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 3...3
            (D) OTHER INFORMATION: Xaa = Lys or Arg (xi) SEQUENCE DESCRIPTION: SEQ ID NO: 107:

Arg Xaa Xaa Arg Xaa
 1               5
```

(2) INFORMATION FOR SEQ ID NO: 108:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 108:

Asn Leu Thr Arg Ile
1               5

(2) INFORMATION FOR SEQ ID NO: 109:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 109:

Ile Lys Pro Arg Ile
1               5

(2) INFORMATION FOR SEQ ID NO: 110:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 110:

Ser Met Thr Arg Ile
1               5

(2) INFORMATION FOR SEQ ID NO: 111:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 111:

Pro Gln Gly Arg Ile
1               5

(2) INFORMATION FOR SEQ ID NO: 112:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 112:

Met Lys Thr Arg Ile
1               5

(2) INFORMATION FOR SEQ ID NO: 113:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 113:

Ile Glu Gly Arg Ile
1               5

(2) INFORMATION FOR SEQ ID NO: 114:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 114:

Arg Arg Lys Arg Ile
1               5

(2) INFORMATION FOR SEQ ID NO: 115:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 115:

Arg Val Arg Arg Ile
1               5

(2) INFORMATION FOR SEQ ID NO: 116:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 116:

Arg Arg Arg Arg Ile
1               5

(2) INFORMATION FOR SEQ ID NO: 117:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 117:

```
Arg Pro Lys Arg Ile
 1               5
```

(2) INFORMATION FOR SEQ ID NO: 118:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 118:

```
Ile Arg Lys Arg Ile
 1               5
```

(2) INFORMATION FOR SEQ ID NO: 119:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 119:

```
Arg Ser Lys Arg Ile
 1               5
```

(2) INFORMATION FOR SEQ ID NO: 120:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 120:

```
Arg Val Thr Arg Ile
 1               5
```

(2) INFORMATION FOR SEQ ID NO: 121:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 121:

```
Arg Leu Lys Arg Ile
 1               5
```

(2) INFORMATION FOR SEQ ID NO: 122:

(i) SEQUENCE CHARACTERISTICS:
        (A) LENGTH: 5 amino acids
        (B) TYPE: amino acid
        (C) STRANDEDNESS: single
        (D) TOPOLOGY: linear -continued

```
(ii) MOLECULE TYPE: peptide (xi) SEQUENCE DESCRIPTION: SEQ ID NO: 122:

Thr Ser Thr Arg Ile
1               5
```

FACTOR X ANALOGUES WITH A MODIFIED PROTEASE CLEAVAGE SITE

CROSS-REFERENCES TO RELATED APPLICATIONS

This application is the U.S. national phase of PCT/AT98/00045, filed Feb. 27, 1998, which claims priority to Austrian Application A335/97, filed Feb. 27, 1997.

FIELD OF INVENTION

The invention relates to Factor X analogues having a modification in the region of the activation peptide, to a preparation containing the Factor X analogues according to the invention, and to a method of preparing single chain and double chain Factor X analogues.

BACKGROUND

After the blood coagulation process has been initiated, the coagulation cascade continues through sequential activation of various proenzymes (zymogens) in the blood to their active forms, the serine proteases. Among them are, inter alia, Factor XII/XIIa, Factor XI/XIa, Factor IX/IXa, Factor X/Xa, Factor VII/VIIa and prothrombin/thrombin. In their physiological state, most of these enzymes are only active if associated to a membrane surface in a complex. Ca ions are involved in many of these processes. The blood coagulation will either follow the intrinsic pathway, wherein all protein components are present in the blood, or the extrinsic pathway, wherein the cell membrane tissue factor plays a critical role. Finally, the wound will be closed by thrombin cleaving fibrinogen to fibrin.

The prothrombinase complex is responsible for activating prothrombin to thrombin. Thrombin is an important enzyme which can act as a procoagulant as well as an anticoagulant. The prothrombinase complex, in which, inter alia, Factor Va (as cofactor) and Factor Xa (as serine protease) are involved, assembles in a Ca-dependent association at the surface of phospholipids. It is discussed that Factor Xa is the catalytic component of the prothrombinase complex.

Factor X (Stuart-Prower factor) is a vitamin K-dependent coagulation glycoprotein by which the intrinsic and the extrinsic blood coagulation cascades can be activated. The primary translation product of Factor X (pre-pro-FX) has 488 amino acids and is initially synthesized by the liver or human hepatoma cells as a single-chain 75 kD precursor protein. In plasma, Factor X is largely present as a double chain molecule (Fair et al., 1984, Blood 64:194–204).

During biosynthesis, after cleavage of the presequence by a signal peptidase (between Ser23/Leu24) and of the propeptide (between Arg40/Ala41), the single chain Factor X molecule is cleaved by processing and removal of the tripeptide Arg180-Lys181-Arg182 to the double chain form consisting of the approximately 22 kD light chain and the approximately 50 kD heavy chain, which are connected via a disulfide bridge (FIGS. 1A–1B). Therefore, Factor X circulates in the plasma as a double chain molecule.

During the blood coagulation process, Factor X is converted from inactive zymogen to active protease Factor Xa by limited proteolysis; wherein Factor X can be activated to Factor Xa in either of two membrane-associated complexes: in the extrinsic Factor VIIa-tissue factor complex or in the intrinsic Factor VIIIa-Factor IXa-phospholipid-Ca-complex, or "tenase complex" (Mertens et al., 1980, Biochem. J. 185:647–658). A proteolytic cleavage between amino acids Arg234/Ile235 results in the release of an activation peptide having a length of 52 amino acids from the N-terminus of the heavy chain and thus to the formation of the active enzyme, Factor Xa. The catalytic center of Factor Xa is located on the heavy chain.

Activation via the Factor VIIa-TF (extrinsic) complexresults in the formation of Factor Xaα (35 kD) and Factor Xaβ (31 kD), with a polypeptide of 42 (kD) forming, too, if, the Factor VIIa concentration in the complex is low. Factor Xaα is formed by a cleavage at Arg234/Ile235 of the heavy chain and represents the activation of Factor X to Factor Xa. The occurence of Factor Xaβ presumably results from an autocatalytic cleavage at Arg469/Gly470 in the C-terminus of the heavy chain of Factor Xaα and the removal of a 4.5 kD peptide. Like Factor Xaα, Factor Xaβ has catalytic activity. It has been shown, however, that a plasminogen binding site is formed by the cleavage of Factor Xaα to Factor Xaβ, and that Factor Xaβ optionally has fibrinolytic activity or is involved in fibrinolysis as a cofactor. The conversion of Factor Xaα to Factor Xaβ, however, is slower than the formation of thrombin, thus preventing the initiation of fibrinolysis before a blood clot is formed (Pryzdial et al., 1996, J. Biol. Chem. 271:16614–16620; Pryzdial et al., 1996, J. Biol. Chem. 271:16621–16626).

The 42 kD polypeptide results from processing in the C-terminus of the heavy chain between Arg469/Gly470 without previous processing between Arg234/Ile235. Like a Factor Xaγ fragment formed by proteolysis at Lys370, this intermediate has no catalytic activity (Mertens et al., 1980, Biochem. J. 185:647–658; Pryzdial et al., 1996, J. Biol. Chem. 271:16614–16620).

Intrinsic Factor X activation is catalysed by the Factor IXa-Factor VIIIa complex. The same processing products are obtained during activation, but the Factor Xaβ product is obtained in larger quantity than other Factor X processing products (Jesty et al., 1974, J. Biol. Chem. 249:5614).

In vitro, Factor X can, for instance, be activated by Russell's viper venom (RVV) or trypsin (Bajaj et al., 1973, J. Biol. Chem. 248:7729–7741) or by purified physiological activators, such as FVIIa-TF complex or Factor IXa-Factor VIIIa complex (Mertens et al., 1980, Biochem. J. 185:647–658).

Most commercially available Factor X products from plasma contain a mixture of Factor Xaα and Factor Xaβ, because after activation of Factor X to Factor Xa mainly Factor Xaα is formed, which is, in turn, cleaved to Factor Xaβ in an autocatalytic process. In order to produce a uniform Factor Xa product having high structural integrity, EP 0 651 054 suggested to activate Factor X with RVV over an extended period of time so that the resulting final product substantially contains Factor Xaβ. The by-products, e.g. Factor Xaα, as well as the protease were subsequently removed by several chromatographic steps.

Factor X cDNA has been isolated and characterized (Leytus et al., 1984, Proc. Natl. Acad. Sci., U.S.A., 82:3699–3702; Fung et al., 1985, Proc. Natl. Acad. Sci., U.S.A., 82:3591–3595). Human Factor X has been expressed in vitro in various types of cells, such as human embryonal kidney cells or CHO cells (Rudolph et al., 1997, Prot. Expr. Purif. 10:373–378; Wolf et al., 1991, J. Biol. Chem. 266:13726–13730). However, it has been found that in the recombinant expression of human Factor X, the processing at position Arg40/Ala41is inefficient, as opposed to the situation in vivo, and that different N-termini at the light chain of Factor X are produced (Wolf et al., 1991, J. Biol. Chem. 266:13726–13730). Recombinant Factor X (rFX) was activated to rFactor Xa (rFXa) by RVV in vitro, or rFXa was expressed directly, with the activating peptide being deleted from amino acid 183 to amino acid 234 and replaced by a tripeptide in order to allow processing directly to a double chain rFXa form. About 70% of purified rFX was processed into light and heavy chain, while the remaining 30% represented single chain rFX of 75 kD. Direct expression of rFXa did result in the formation of active Factor Xa, but also of inactive intermediates. Wolf et al. (1991, J. Biol. Chem. 266:13726–13730) detected still reduced activity of recombinant Factor X, which they ascribed to the poorer ability of rFX to be activated by RVV and to the inactive protein and polypeptide populations of the single chain precursor molecule. In particular, they found high rFXa instability when expressed by recombinant cells, which they ascribed to the high rate of autoproteolysis.

In order to study the function of the C-terminal peptide of Factor Xaα, Eby et al. (1992, Blood 80 (Suppl. 1):1214 A) introduced a stop codon at position Gly430 of the Factor X sequence. However, they did not find a difference between the rate of activation of Factor Xa (FXaα) by β-peptide or a deletion mutant without β-peptide (FXaβ).

Factor Xa is an important component of the prothrombinase complex and might therefore be used to treat patients suffering from blood coagulation disorders, e.g. hemophilia. Particularly the treatment of hemophilia patients suffering from Factor VIII or Factor IX deficiency with factor concentrates produced from plasma is often complicated by the formation of inhibiting antibodies against these factors in long-term therapy. Therefore, a number of alternatives have been developed to treat hemophiliacs with factors having bypass activity. The use of prothrombin complex concentrate, partially activated prothrombinase complex (APPC), Factor VIIa or FEIBA has been suggested. Commercial preparations with Factor VIII bypass activity (FEIBA) are, for instance, FEIBA® or Autoplex®. FEIBA® contains comparable units of Factor II, Factor VII, Factor IX, Factor X and FEIBA, small amounts of Factor VIII and Factor V, and traces of activated coagulation factors, such as thrombin and Factor Xa or a factor having Factor X-like activity (Elsinger, 1982, Activated Prothrombin Complex Concentrates. Ed. Mariani, Russo, Mandelli, pp. 77–87). Elsinger particularly points at the importance of a "Factor Xa-like" activity in FEIBA®. Factor VIII bypass activity was shown by Giles et al (1988, British J. Haematology 9:491–497) for a combination of purified Factor Xa and phospholipids in an animal model.

Therefore, Factor X/Xa or Factor X/Xa-like proteins, either alone or as a component of a coagulation complex, are in high demand and can be used in various fields of application in hemostasis therapy.

In vivo as well as in vitro, the half-life of Factor Xa is considerably shorter than the half-life of the zymogen. For instance, Factor X can be stored stably in glycerol for 18 months, while Factor Xa is stable for only 5 months under the same conditions (Bajaj et al., 1973, J. Biol. Chem. 248:7729–7741) and shows reduced activity by more than 60% after 8 months in glycerol at 4° C. (Teng et al., 1981, Thrombosis Res. 22:213–220). The half-life of Factor Xa in serum is a mere 30 seconds.

Because Factor Xa is instable, the administration of Factor X preparations has been suggested (U.S. Pat. No. 4,501,731). If, however, the bleeding is so serious that the patient might die, particularly in hemophiliacs, the administration of Factor X is ineffective, because owing to the functional "tenase complex" deficiency in the intrinsic pathway of blood coagulation, Factor X can not be sufficiently activated to Factor Xa, and activation via the extrinsic pathway is often too slow to show effects quickly. Moreover, hemophiliacs have sufficient amounts of Factor X, but its prothrombinase activity is 1000 times less than that of Factor Xa. In such cases it is necessary to administer activated Factor Xa directly, optionally in combination with phospholipids, as described in Giles et al. (1988, British J. Haematology 9:491–497) or with other coagulation factors, e.g. with Factor VIII bypass activity.

In the preparation of Factor Xa from Factor X, activation has so far mostly been carried out by nonphysiological activators of animal origin, such as RVV or trypsin, and it was necessary to make absolutely sure that the final product is completely free of these proteases. As mentioned above, when Factor X is activated to Factor Xa, quite a number of intermediates, some of them inactive, are formed (Bajaj et al., 1973, J. Bio. Chem. 248:7729–7741; Mertens et al., 1980, Biochem. J. 185:647–658). The presence of such intermediates results in reduced specific activity of the product and may produce intermediates which can function as active serine protease antagonists. Therefore, the preparation of a uniform, pure product having high specific activity according to conventional methods requires complex processes of activation and chromatographic purification.

SUMMARY

Thus, the aim of the present invention is to provide a preparation containing a polypeptide having Factor X/Xa activity which exhibits high stability and can be activated to Factor Xa without using any of the conventional proteases, particularly those of animal origin, such as, for instance, RVV or trypsin. Another aim is to provide a pharmaceutical preparation having Factor VIII bypass activity.

According to the present invention, the aim is reached by providing a Factor X analogue having a modification in the region of the natural Factor Xa activation cleavage site. The modification in the region of the activation cleavage site is a novel recognition andprocessing site for a protease which site is not naturally located at this position in the polypeptide, which protease would not usually cleave the polypeptide at this site.

BRIEF DESCRIPTION OF THE DRAWINGS

FIGS. 1A and 1B: nucleotide and amino acid sequence of Factor X (SEQ ID NOS:26 and 27).

FIGS. 5A and 5B: Western blot analysis of rFactor X after in vitro cleavage by furin derivatives.

DETAILED DESCRIPTION

Figure 2A:
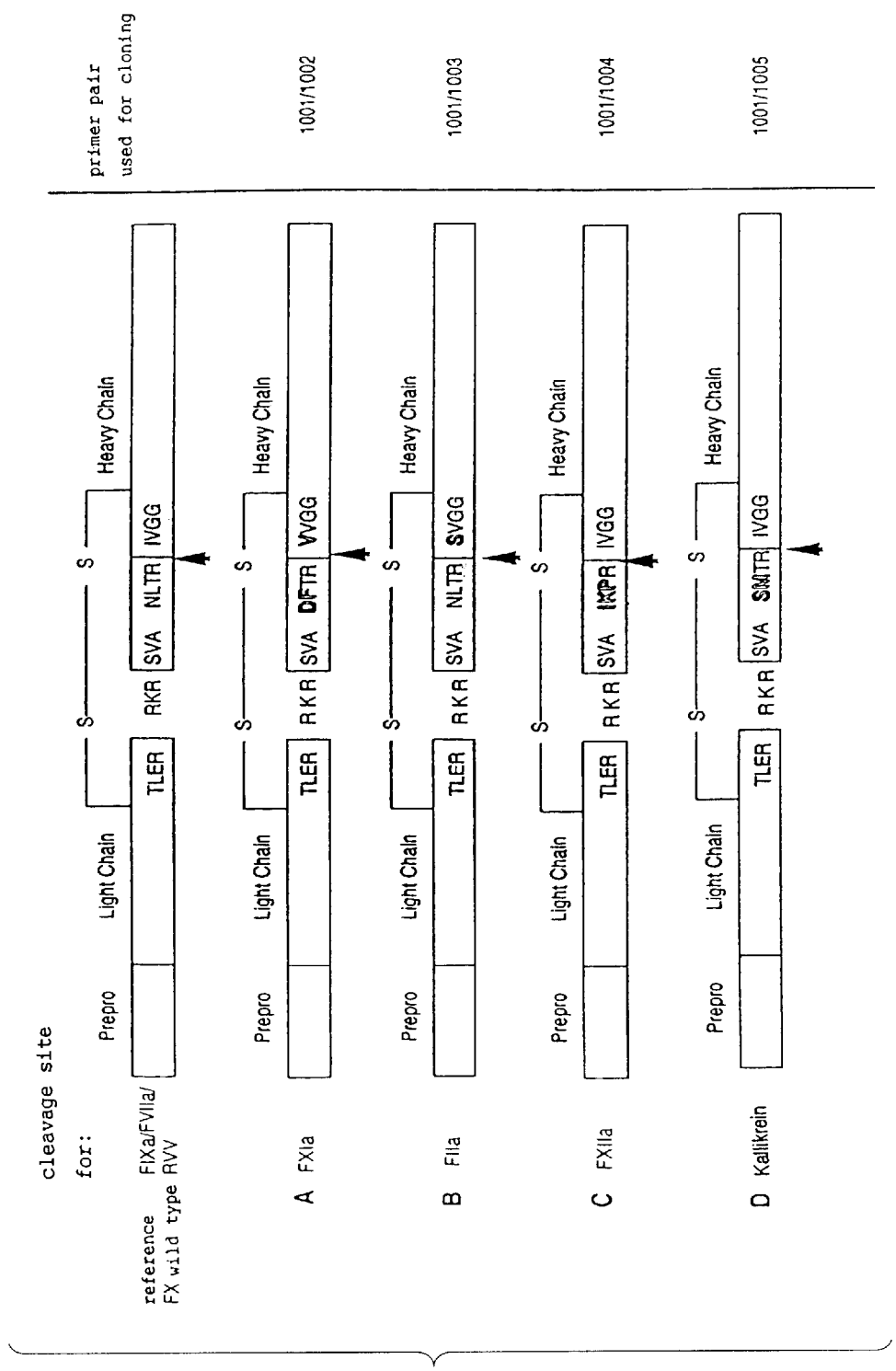
FIGS. 2A and 2B: schematic representation of the Factor X analogues having modified protease cleavage sites in the region of the activation peptide (SEQ ID NOS:77–95).

The Factor X analogue according to the invention is modified particularly in the activation peptide which is removed when Factor X is activated to Factor Xa. At least one amino acid within the amino acid sequence of the activation peptide of Factor X is modified. Said modification is particularly located in the C-terminal region of the activation peptide and represents, at least, an exchange of at least one amino acid between position Gly228 and Arg234 of the Factor X amino acid sequence. The position of amino acids is based on the numbering according to the sequence shown in FIGS. 1A–1B, starting with Metl and ending with Lys488.

Said modification in the Factor X analogue according to the present invention is preferably an exchange of a Factor VIIa/Factor IXa processing site located at this position for an alternative cleavage site of a different protease. The modification can be a substitution of at least one amino acid, or an insertion of a peptide sequence representing a protease recognition or cleavage site. In the Factor X analogue according to the invention, the modification is preferably such that it represents a detection or cleavage sequence for a protease from the group of endoproteases, such as kexin/Kex2, furin/PACE, PC1/PC3, PC2, PC4, PACE 4, LPC/PC7 (as described in Barr et al., 1991, Cell 66:1–3 or in U.S. Pat. No. 5,460,950), of serine proteases, such as Factor XIIa, Factor XIa, Factor IIa, Factor Xa, or of kallikrein, or of a derivative of these proteases.

Preferably, the modification is selected such that processing by one of these proteases leads to a polypeptide corresponding to native Factor Xa, which is substantially equal to the natural Factor Xa sequence and also displays Factor Xa activity.

For optimal processing, it may be necessary in individual cases to exchange the amino acid Ile235, too. Preferably, however, the $NH_2$ terminal amino acid isoleucin of the heavy chain should still be present after activation, because this amino acid performs an essential function in the formation of the substrate binding pocket (Watzke et al., 1995, Molecular Basis of Thrombosis and Hemostasis, ed. Katherine High & Harold Roberts). The Factor X analogues according to the invention have a structural difference, particularly on the amino acid level, as compared to a native Factor X sequence, but they can be activated similarly to natural Factor X and have Factor Xa activity after activation.

The invention provides an exemplary number of Factor X analogues having a modification in the activation peptide relative to the natural Factor X sequence and different protease specificity.

Modifications can be located at one or more positions in the region between amino acid Gly228 and Arg234, and optionally Ile235, based on the Factor X sequence numbered Met1 to Lys488 according to FIGS. 1A–1B. Amino acid substitutions can be at positions Ile235 (R1), Arg234, Thr233 (R2), Leu232 (R3), Asn231 (R4), Asn230 (R5) and Asp229 (R6), with Arg 234 preferably remaining unchanged.

Preferably, the Factor X analogues according to the invention contain a Factor X sequence with Gly228-R6-R5-R4-R3-R2-Arg234-R1 (SEQ ID NO:28), wherein R1=Ile, Val, Ala, Ser or Thr; R2=Thr, Pro, Gly, Lys or Arg; R3=Leu, Phe, Lys, Glu, Met, Gln, Ser, Val Arg or Pro; R4=Asn, Asp, Ile, Ser, Met, Pro, Thr, Lys or Arg; R5=Asn, Lys, Ser, Glu, Ala, Gln, His or Arg; and R6=Asp, Phe, Thr, Arg, Leu or Ser.

Preferred embodiments of the Factor X analogues according to the invention are Factor X analogues having a modification with a) R1=Val, R2=Thr, R3=Phe, R4=Asp, R5=Asn and optionally R6=Phe (FIG. 2A, Panel A) (SEQ ID NO:29 and 30), and processed by Factor XIa;

b) R1=Ser, R2=Thr, R3=Leu, R4=Asn (FIG. 2A, Panel B) (SEQ ID NO:31), and processed by Factor IIa;

c) R1=Ile, R2=Pro, R3=Lys, R4=Ile, and optionally R5=Lys and/or R6=Thr (FIG. 2A, Panel C) (SEQ ID NOS:32–35), or R1=Ile, R2=Thr, R3=Ser, R4=Thr, and optionally R5=Lys and/or R6=Thr (FIG. 2B, Panel I) (SEQ ID NOS:36–39), and processed by Factor XIIa;

d) R1=Ile, R2=Thr, R3=Met, R4=Ser, and optionally R5=Ser and/or R6=Leu (FIG. 2A, Panel D) (SEQ ID NOS:40–43), and processed by kallikrein;

e) R1=Ile, R2=Gly, R3=Gln, R4=Pro, and optionally R5=Lys and/or R6=Ser (FIG. 2B, Panel H) (SEQ ID NOS:44–47), or R1=Ile, R2=Thr, R3=Lys, and R4=Met (FIG. 2B, Panel E) (SEQ ID NO:48), or R1=Ile, R2=Gly, R3=Glu, and R4=Ile (FIG. FIG. 2B, Panel F) (SEQ ID NO:49), and processed by Factor Xa;

f) R1=Ile, R2=Lys, R3=Arg, R4=Arg, and optionally R5=Glu and/or R6=Leu (SEQ ID NOS:50–53), or R1=Ile, R2=Thr, R3=Val, R4=Arg, and optionally R5=Ala and/or R6=Leu (SEQ ID NOS:54–57), or R1=Ile, R2=Arg, R3=Val, R4=Arg, and optionally R5=Gln and/or R6=Leu (SEQ ID NOS:58–61), or R1=Ile, R2=Arg, R3=Arg, R4=Arg, and optionally R5=His and/or R6=Leu (SEQ ID NOS:62–65), or R1=Ile, R2=Lys, R3=Pro, R4=Arg, and optionally R5=Asn and/or R6=Leu (SEQ ID NOS:66 and 67), or R1=Ile, R2=Lys, R3=Arg, R4=Ile, and optionally R5=Arg and/or R6=Leu (SEQ ID NOS:68–71), or R1=Ile, R2=Lys, R3=Ser, and R4=Arg (SEQ ID NO:72), or R1=Ile, R2=Thr, R3=Val, and R4=Arg (SEQ ID NO:73), or R1=Ile, R2=Lys, R3=Leu, and R4=Arg (SEQ ID NO:74) (all see FIG. FIG. 2B, Panel G), with those mentioned under f) being processed by a dibasic endoprotease, such as furin, PACE, kexin/Kex2, furin/PACE, PC1/PC3, PC2, PC4, PACE 4, LPC/PC7, or by a derivative of one of these proteases.

FIGS. 2A–2B, Panels A-I show a possible selection of modifications and amino acid exchanges leading to a different protease specificity.

The modifications can by carried out by, for instance, directed in vitro mutagenesis or PCR or other methods of genetic engineering known from the state of the art which are suitable for specifically changing a DNA sequence for directed exchanges of amino acids.

According to the present invention, the Factor X analogue according to the invention is activated to native Factor Xa or a Factor Xa analogue preferably by a protease selected from the group of endoproteases, such as kexin/Kex2, furin/PACE, PC1/PC3, PC2, PC4, PACE 4, LPC/PC7, the group of of serine proteases, such as Factor XIIa, Factor XIa, Factor Xa, Factor IIa, or kallikrein, or a derivative of these proteases.

One of the difficulties in the preparation of active Factor Xa is its instability, because apart from Factor Xaα and Factor Xaβ, other, inactive intermediates are formed by autocatalysis. For the preparation of essentially intact, active Factor X/Xa and Factor X/Xa-like molecules, respectively, it would therefore be desirable to obtain only such proteins which result in stable final products.

It is well known that a preferred cleavage site for the processing of Factor Xaα (FXaα) to Factor Xaβ (FXaβ) is between Arg469/Gly470. Based. on research by Eby et al. (1992, Blood. Vol. 80, Suppl., 1, 1214), next to a prominent carboxy-terminal peptide (amino acid residues 476–487) of Factor X, other, shorter peptides (amino acid residues 474–477) are found which are formed by autocatalysis of Factor Xaα. In order to focus directed processing of intact Factor X to i-i essentially active Factor Xa without obtaining inactive processing intermediates, the Factor X analogues of the invention optionally have further modifications.

Therefore, according to a particular embodiment, the Factor X analogue according to the invention has one further modification in the C-terminal region of the Factor X amino acid sequence.

According to one embodiment, a Factor X analogue as described above has an intact β-peptide (FXα). The Factor X analogue according to the invention particularly has a modification in the region of the C-terminal β-peptide cleavage site which prevents cleavage of the β-peptide from Factor X after activation of Factor X to Factor Xa. Thus a Factor Xa molecule is obtained which can be isolated up to 100% as intact Factor Xaα molecule.

The modification can be a mutation, deletion or insertion in the region of the Factor X amino acid sequence between amino acid positions Arg469 and Ser476 and optionally of Lys370. However, an amino acid substitution is preferred which prevents the polypeptide from misfolding as a consequence of the amino acid exchange, which would influence the structure and thus possibly the function and activity of the protein.

According to one embodiment, the Factor X analogues of the invention have one of the amino acids at position Arg469 and/or Gly470 exchanged, with Arg469 being preferably exchanged for Lys, His or Ile, and Gly470 being preferably exchanged for Ser, Ala, Val or Thr.

Besides a mutation at position Arg469 and/or Gly470, the Factor k analogues according to the invention can have another mutation at position Lys370 and/or Lys475 and/or Ser476.

Amino acid substitution at one of these positions prevents processing of Factor Xaα to Factor Xaβ or Factor Xaγ, respectively, because the natural processing sequence(s) is (are) modified such that an occasional autocatalytic cleavage of the carboxy-terminal peptide becomes impossible.

According to a further embodiment, the Factor X analogue of the invention has a deleted carboxy-terminal β-peptide (FXβ). Such a Factor X analogue can be prepared by expressing a cDNA encoding a Factor X analogue in a recombinant expression system, cloning only those sequences that encode the amino acids Met1 to Arg469.

According to a further embodiment, the Factor X analogue according to the invention has a translation stop signal in the C-terminal region of the Factor X sequence. This translation stop signal is preferably located at a position following a C-terminal amino acid formed after natural processing. Therefore, the translation stop signal is preferrably at the position of amino acid 470 of the Factor X sequence, so that the terminal Arg469 of Factor Xaβ is retained. For this purpose, the codon GGC encoding amino acid Gly470 is substituted by TAA, TAG or TGA.

Another aspect of the present invention relates to Factor X analogues which are activated to native Factor X or Factor Xa anlogues by treatment with an appropriate protease in vitro. Depending on the Factor X analogue used and activated, a polypeptide which corresponds to native Factor Xa and is essentially identical, or a polypeptide having Factor Xa activity but having modifications relative to the native Factor Xa sequence which, however, do not limit its biological activity are obtained. When Factor X analogues are activated which are modified in the region of the activation peptide in the sequence of the activation peptide, only polypeptides corresponding to native Factor Xa molecules are obtained. If such a Factor X analogue additionally has a translation stop signal in the C-terminal region of the β-peptide, Factor Xaβ homologous molecules are obtained. If, however, Factor X analogue is employed which has modification(s) within the β-peptide sequence resulting in the β-peptide not being cleaved off, a Factor Xaα analogue with an amino acid exchange in the C-terminus of the molecule is obtained.

The Factor X analogues of the invention only have modifications which change the specificity for the ability to be activated and do not influence the activity. Therefore, in any case, biologically and functionally active Factor Xa molecules or Factor Xa analogues, respectively, are obtained.

In vitro activation can be effected by a protease selected from the group of endoproteases, such as kexin/Kex2, furin/PACE, PC1/PC3, PC2, PC4, PACE 4, LPC/PC7, the group of serine proteases, such as Factor IIa, Factor XIIa, Factor XIa, Factor Xa, or kallikrein, or a derivative of these proteases. It is within the scope of the present invention to use any protease, except RVV, trypsin, Factor IXa or Factor VIIa, as long as it is apt to process the Factor X analogue of the invention to Factor Xa.

According to a further embodiment of the invention, the Factor X analogue contains a modification allowing activation of the Factor X analogue to Factor Xa, preferably native Factor Xa, in vivo. In this context, "native" Factor Xa means that thelactivated Factor Xa, derived from the Factor X analogue according to the invention, has an amino acid sequence corresponding to and homologous with native Factor Xa, and has Factor Xa activity. Said modification is chosen such that Factor X is processed to Factor Xa by a protease present in vivo, i.e. in the body, preferably a protease present in the blood coagulation cascade. The protease can be a protease selected from the group of serine proteases, such as Factor XIIa, Factor XIa, Factor Xa, Factor IIa or kallikrein. Factor X analogues having a modification in the C-terminal region of the Factor X molecule apart from the modification in the activation peptide are activated to the corresponding Factor Xa analogue in vivo, too, as described above.

Although Wolf et al. (1991, J. Biol. Chem. 266:13726–137309), for instance, have assumed that an endopeptidase, such as Kex2, furin or PACE, is involved in the processing of the Factor Xa deletion mutant described by this group, they do not give a hint as to the influence of one of these proteases on the processing of Factor X. Similarly, U.S. Pat. No. 5,660,950 describes the recombinant preparation of PACE and the use of the protease to improve processing of vitamin K-dependent proteins. In a long list of blood factors, Factor X is mentioned among others, but no data are provided to verify this statement.

The present invention demonstrates unambiguously for the first time that a protease necessary for the maturation process of Factor X is a dibasic endoprotease, particularly endogenous furin. In vivo, the endoprotease mainly mediates the cleavage of the single chain Factor X molecule to the mature form consisting of heavy and light chain. In vitro, it also mediates the cleavage of the Factor X propeptide sequence (Example 2).

Factor X analogues according to the present invention having a protease cleavage site for a protease not naturally existing in a cell are cleaved by selective processing reactions only at those sites which are also cleaved in native Factor X. Thus, recombinant Factor X molecule is obtained which consists only of the 22 kD light chain and the approximately 50 kD heavy chain and has no inactive Factor X molecules as formed by nonspecific processing. Similar to native Factor X molecules, these modified Factor X molecules are not activated to Factor Xa by intracellular protease. They are activated to Factor Xa only afterwards by the appropriate proteases (i.e. preferentially serine protease or subtilisin-related proteases).

Thus a double chain Factor X analogue is provided according to one embodiment.

According to a particular embodiment, a Factor X analogues are provided which are preferably present in purified form as single chain molecules. By expressing Factor X analogues in a cell deficient of dibasic protease, pro-Factor X is obtained as a single chain molecule. The single chain Factor X molecule is characterized by high stability and molecular integrity. So far, a single chain Factor X molecule could not be isolated in purified form, because it is quickly processed to the double chain form (Fair et al., 1984, Blood 64:194–204). The recombinant single chain Factor X analogues can be processed by specific processing to the double chain Factor X form and subsequently activated to Factor Xa or Factor Xa analogue, respectively. This can be accomplished by bringing into contact a single chain recombinant Factor X molecule isolated from a protease deficient cell and a dibasic protease, such as furin/PACE or Kex2, and processing to a double chain Factor X analogue.

Double chain Factor X analogue can be activated to Factor Xa or Factor Xa analogue, respectively. This can be effected, for instance, by isolating a Factor X analogue having a furin-specific cleavage site due to a modification in the region of the activation peptide, from a furin deficient cell as a single chain molecule and subsequently processing it to an activated Factor Xa molecule by bringing it into contact with this endoprotease.

Likewise, an isolated single chain Factor X analogue having a modification in the activation peptide which allows an alternative processing by a protease from the group of serine proteases or kallikrein can only be cleaved to give a double chain Factor X molecule by treating it with a dibasic endoprotease, such as furin, which double chain Factor X molecule in the further course of events can be brought into contact with a serine protease in such a way that activation to Factor Xa or Factor Xa analogue, respectively, occurs.

A Factor X analogue isolated from cell culture as a double chain molecule can be treated with the protease specific for activation.

Due to the selective and directed processing reaction, a Factor X or Factor Xa analogue thus obtained has high stability and structural integrity and, in particular, is free of inactive Factor X/Xa analogue intermediates and autoproteolytic degradation products.

A further aspect of the present invention relates to recombinant DNA encoding for the Factor X analogues of the invention. The recombinant DNA results after expression in a Factor X analogue with an amino acid sequence corresponding to human Factor X except for a modification influencing the processing specificity and processing products, whereas the biological coagulant acitvity basically remains unchanged.

According to a further aspect, also transformed cells containing the recombinant DNA are provided.

A further aspect of the invention relates to a preparation containing a purified Factor X analogue or a precursor protein thereof having a modification in the region within the natural Factor Xa activation site. The modification in the region of the activation cleavage site is a novel recognition and cleavage site not naturally located at this position in the polypeptide for a protease which usually does not process the polypeptide at this position. The preparation can be a purified preparation of single chain or double chain Factor X analogue; the polypeptide can be obtained from a cell culture system either after isolation from the cell culture supernatant or from a cell culture extract. A recombinant Factor X analogue prepurified from a cell culture system can be further purified by methods known from prior art. Chromatographic methods are particularly suitable for this purpose, such as gel filtration, ion exchange or affinity chromatography.

According to one embodiment, the preparation according to the present invention contains the Factor X analogue as a single chain molecule in isolated form. Such a preparation is prepared by isolating a Factor X analogue, obtained by recombinant preparation, as a single chain molecule from the cell system, preferably a cell culture of cells which lack the endoprotease that processes the single chain molecule into heavy and light chains.

According to a particular aspect, the preparation contains single chain Factor X analogue having a modification allowing in vitro activation to Factor Xa by one of the proteases selected from the group of dibasic endoproteases, such as kexin/Kex2, furin/PACE, PC1/PC3, PC2, PC4, PACE 4, LPC/PC7. The activation is effected by bringing the Factor X analogue into contact with the protease, through which due to the natural processing, a cleavage to the mature Factor X form is effected, and because of the modification, the activation peptide is cleaved off and Factor Xa or Factor Xa analogue are formed.

In the preparation according to the invention, the Factor X analogue as a single chain molecule can be present either as Factor Xα (FXα) or with a deletion of the β-peptide. The preparation particularly contains Factor X analogue in enzymatically inactive form and has a purity of at least 80%, preferably at least 90%, particularly preferably at least 95%, and does not contain any inactive, proteolytic intermediates of Factor X/Xa analogue.

According to a further embodiment, the preparation according to the present invention contains the Factor X analogue preferably as a double chain molecule in isolated form. For this purpose, Factor X analogue, for instance, obtained by recombinant preparation as a single chain molecule from a cell system, is cleaved in vitro, i.e. outside the cell, by a protease, preferably a dibasic protease, to the double chain form. This can be effected by mixing the protease directly with the culture supernatant of the clones expressing Factor X analogues, either by mixing the purified protease or a cell culture supernatant of a cell culture expressing the protease in recombinant form, or by co-cultivation of Factor X analogue and protease expressing clones.

Similarly, the cell culture supernatant containing the Factor X analogue or the purified Factor X analogue can be brought into contact with an immobilized protease, whereby processing to the double chain form occurs. In this process, the protease is preferably bound to a matrix, and the cell culture supernatant or a purified preparation containing the Factor X analogue is passed over this matrix. However, it is also possible to immobilize the Factor X analogue while the protease is in the mobile phase. Similarly, the reactants (Factor X analogue and protease) can be mixed and incubated over a certain period of time. Subsequently, the protease is removed from the mixture, e.g. by affinity chromatography.

The double chain form of the Factor X analogue can also be obtained by co-expressing protease and Factor X analogue directly in a given cell and optionally purifying it.

According to a particular embodiment of the invention, the preparation contains a single chain or double chain Factor X analogue having a modification allowing activation to Factor Xa or Factor Xa analogue in vitro. The activation of Factor X analogue to Factor Xa or Factor Xa anlogue, respectively, can be effected by bringing the Factor X analogue into contact with a protease selected from the group of dibasic endoproteases, auch as kexin/Kex2, furin/ PACE, PC1/PC3, PC2, PC4, PACE 4, LPC/PC7, the group of serine proteases, such as Factor XIIa, Factor XIa, Factor IIa, Factor Xa, or kallikrein, or a derivative of these proteases. The protease can be immobilized on a carrier.

The preparation according to the invention can serve as a starting material for the preparation and production of Factor Xa. For large-scale preparation, the preparation containing single chain or double chain Factor X anlogue is, for instance, brought into contact with optionally immobilized protease under conditions allowing optimal activation of Factor X analogue to Factor Xa, and Factor Xa or Factor Xa analogues are obtained. The Factor Xa/Xa analogue thus yielded can subsequently be formulated to a pharmaceutical composition according to generally known methods.

According to a particular embodiment, the preparation containing the purified, single chain or double chain Factor X analogue contains a physiologically acceptable carrier and is optionally formulated as a pharmaceutical preparation. The formulation can be effected according to a method common per se, and it can be mixed with a buffer containing salts, such as NaCl, $CaCl_2$, and amino acids, such as glycine and/or lysin, at a pH in the range of 6 to 8, and formulated as a pharmaceutical preparation. The purified preparation containing Factor X analogue can be provided as a storable product in the form of a ready-made solution, lyophilisate or deep frozen until final use. Preferably, the preparation is stored in lyophilized form and dissolved with an appropriate reconstitution solution to an optically clear solution.

The preparation according to the present invention can also be provided as a liquid preparation or in the form of deep frozen liquid.

The preparation according to the present invention is particularly stable, i.e. it can be left standing in dissolved form over an extended period of time before application. The preparation according to the invention has proven to show no loss in activity for several hours up to days.

The preparation according to the invention can be provided in an appropriate device, preferably an application device, in combination with a protease selected from the group of endoproteases, such as kexin/Kek2, furin/PACE, PC1/PC3, PC2, PC4, PACE 4, LPC/PC7, the group of serine proteases, such as Factor IIa, Factor XIIa, Factor XIa, Factor Xa, or kallikrein, or a derivative of these proteases.

The preparation according to the invention containing a Factor X analogue in combination with a protease able to activate the Factor X analogue to Factor Xa or Factor Xa analogue can be provided as a compound preparation consisting of a container containing a protease immobilized on a carrier, optionally in the form of a small column or a syringe equipped with a protease and a container containing the pharmaceutical preparation with Factor X analogue. For activation.of the Factor X analogue, the solution containing Factor X analogue is, for instance, passed over the immobilized protease. During storage of the preparation, the solution containing Factor X analogue is preferably kept apart from the protease. The preparation according to the invention can be present in the same container as the protease, with the components, however, being spatially separated by an impermeable separation wall which can be easily removed in case of use. The solutions can also be stored in individual containers and brought into contact only shortly before application.

In a particular embodiment, the protease used for activation is a serine protease naturally involved in blood coagulation, such as Factor XIIa or Factor XIa, IIa, Xa which need not be separated from activated Factor Xa before application but may be applied together with it.

Factor X analogue can be activated to Factor Xa shortly before immediate use, i.e. before application to the patient. The activation can be effected by bringing it into contact with an immobilized protease or by mixing solutions containing a protease and Factor X analogue, respectively. Thus it is possible to keep the two components in solution apart from each other, to mix them by means of an appropriate infusion device wherein the components get into contact with each other while passing through, and thus to activate the respective molecule to Factor Xa or Factor Xa analogue. The patient will receive a mixture of Factor Xa and a further serine protease which has mediated the activation. Particular care has to be taken in regard of dosage, because endogeneous Factor X may also be activated by the additional administration of a serine protease, which might result in a shorter coagulation time.

According to a preferred embodiment, the pharmaceutical preparation is provided in an appropriate device, preferably an application device, either in frozen liquid or in lyophilized form. An appropriate application device can be a double compartment syringe as described in AT 366 916 or AT 382 783.

According to an aspect of the invention, the preparation contains a Factor X analogue having a modification allowing activation of Factor X analogue to a Factor Xa in vivo. The Factor X analogues of the preparation according to the invention particularly have a modification representing a recognition/cleavage site for a protease selected from the group of serine proteases, such as Factor XIIa, Factor IIa, Factor XIa, Factor Xa, or kallikrein, and are cleaved in vivo by one of said proteases to native Factor Xa or Factor Xa analogue. Particularly for therapeutic use, such Factor X analogues are advantageous which have a recognition/ cleavage site for a protease which is independent from Factor VIIa/tissue complex and tenase complex within the coagulation cascade. Therefore, the preparation according to the invention can be used to control bleeding in patient deficient of Factor IX and Factor VII as well as Factor VIII. Patients suffering from a blood coagulation disorder due to Factor XI or Factor XII deficiency should not be given pharmaceutical preparations containing Factor X analogue which can be activated by Factor XIIa or Factor XIa. In case of Factor XI deficiency, for instance, Factor X analogue having a Factor XIIa cleavage site could be used.

According to another aspect of the invention, the preparation according to the invention optionally contains a blood factor in the form of a zymogen or an active serine protease as a further component. Preferred further components are components having Factor VIII bypass activity. Among them are, in particular, Factor II, Factor VII, Factor IX, Factor VIII, Factor V and/or the active serine proteases thereof. Further components can also be phospholipids, Ca ions etc. According to a particular embodiment of the invention, the preparation according to the invention contains at least one further component having Factor VIII bypass activity.

The preparation according to the invention can be provided as a pharmaceutical preparation having Factor Xa activity as a single component preparation or in combination with other factors as a multiple component preparation.

Before processing into a pharmaceutical preparation, the purified protein is subjected to the usual quality controls and brought into a therapeutically administrable form. In recombinant production, the purified preparation is particularly tested for the absence of cellular and expression vector derived nucleic acids, preferably according to a method as described in EP 0 714 987.

As, in principle, any biological material can be contaminated with infectious agents, the preparation is optionally treated for inactivation or depletion of viruses in order to produce a safe preparation.

According to a further aspect of the present invention, a preparation containing Factor Xa analogue having high stability and structural integrity is provided which is particularly free of inactive Factor X/Xa analogue intermediates and autoproteolytic degradation products, and is obtainable in that a Factor X analogue of the above defined type is activated and prepared to yield the appropriate preparation.

A further aspect of the invention refers to the use of a preparation of the above defined type in the preparation of a pharmaceutical agent. A therapeutic agent containing a Factor X analogue or Factor Xa anlogue according to the invention is particularly useful in the treatment of patients suffering from blood coagulation disorders, such as patients suffering from hemophilia and who, in addition, may have developed inhibitory antibodies against Factor VIII and/or Factor IX, commonly used for treatment, and, in particular, as a preparation having Factor VIII bypass activity.

A further aspect of the invention is related to the use of a nucleic acid containing the encoding sequences of the Factor X analogues according to the invention for the preparation of a medicament. As long as the nucleic acid has appropriate expression control sequences, it can be applied as a naked nucleic acid, integrated into a recombinant expression vector, or bound to a carrier, either a phospholipid or a viral particle. The nucleic acid can be used for the preparation of a therapeutic agent which is particularly useful in the treatment of patients suffering from blood coagulation disorders, such as patients suffering from hemophilia or hemophilia and having developed inhibitory antibodies. It is also possible to use the nucleic acid in gene therapy.

A further aspect of the invention relates to a method for the preparation of the Factor X analogue according to the invention and a preparation containing the Factor X analogue according to the invention. A sequence coding for the Factor X analogue is inserted into an appropriate expression system, and appropriate cells, preferably permanent cell lines, are transfected with the recombinant DNA. The cells are cultivated under optimal conditions for gene expression, and Factor X analogues are isolated either from a cell culture extract or from the cell culture supernatant. The recombinant molecule can be further purified by all known chromatographic methods, such as anion or cation exchange, affinity or immunoaffinity chromatography or a combination thereof.

For the preparation of the Factor X analogues according to the invention, the entire cDNA coding for Factor X is cloned in an expression vector. This is done according to generally known cloning techniques. Subsequently, the nucleotide sequence coding for Factor X is modified such that the encoding sequences in the region of the activation peptide and optionally also in the region of the C-terminal β-peptide are modified such that a Factor X molecule of the above defined type can be produced. This is effected by genetic engineering techniques known from the prior art, such as specific directed in vitro mutagenesis, or deletion of sequences, e.g. by restriction digestion by endonucleases and insertion of other, changed sequences, or by PCR. The Factor X mutants thus prepared are then inserted&into an expression system appropriate for recombinant expression and are expressed.

The Factor X analogues according to the invention can also be prepared by chemical synthesis.

The Factor X analogues are preferably produced by recombinant expression. They can be prepared by means of genetic engineering with any usual expression systems, such as, for instance, permanent cell lines or viral expression systems. Permanent cell lines are prepared by stable integration of the foreign DNA into the host cell chromosome of, e.g., Vero, MRC5, CHO, BHK, 293, Sk-Hep1, particularly liver and kidney cells, or by an episomal vector derived, e.g., from the papilloma virus. Viral expression systems, such as, for instance, Vaccinia virus, Baculovirus or retroviral systems, can also be employed. As cell lines, Vero, MRC5, CHO, BHK, 293, Sk-Hep1, gland, liver and kidney cells are generally used. As eukaryotic expression systems, yeasts, endogenous glands (e.g. glands of transgenic animals) and other types of cells can be used, too. Of course, transgenic animals can also be used for the expression of the polypeptides according to the invention or derivatives thereof. For the expression of the recombinant proteins, CHO-DHFR⁻ cells have proved particularly useful (Urlaub et al., 1980, Proc. Natl. Acad. Sci., U.S.A., 77:4216–4220).

For the recombinant preparation of Factor X analogues according to the invention, prokaryotic expression systems can be used, too. Systems allowing expression in *E. coli* or *B. subtilis* are particularly useful.

The Factor X analogues are expressed in the respective expression systems under control of a suitable promotor. For expression in eucaryotes, all known promoters are suitable, such as SV40, CMV, RSV, HSV, EBV, β-actin hGH or inducible promoters, such as, for instance, hsp or metallothionein promotor. The Factor X analogues are preferably expressed under control of the β-actin promotor in CHO cells.

According to an embodiment of the invention, the method of producing the preparation of the invention comprises the steps of: providing a DNA encoding a Factor X analogue, transforming a cell with the recombinant DNA, expressing the Factor X analogue, optionally in the presence of a protease, isolating the Factor X analogue, and optionally purifying by means of a chromatographic method.

According to an embodiment of the process, the Factor X analogue is isolated as double chain molecule. Factor X analogue is expressed in a cell allowing processing of pro-Factor X analogue to double chain Factor X analogue. The cell is preferably a cell expressing a protease able to process Factor X precursor, e.g. a dibasic protease, such as furin or a derivative thereof. To improve or enhance processing efficiency, the cell can optionally be modified such that its protease expression is enhanced. For instance, this can be effected by co-expression of a corresponding dibasic endoprotease, such as furin/PACE, Kex2 or a derivative thereof. The Factor X analogue according to the invention can also be expressed in a cell having normal endogenous protease concentration, i.e. a suboptimal concentration for processing, resulting in incomplete processing to the double chain form. In this case, as long as single chain Factor X analogue is secreted into the cell supernatant as described above, subsequent processing to light and heavy chain is effected by co-culturing with protease expressing cells or bringing into contact with an optionally immobilized protease. The cell supernatant can also be passed over a carrier matrix having protease bound thereto, thus yielding double chain Factor X analogue in the eluate. The reactants can also be mixed in solution, incubated for a certain period of time, and then the protease can be removed, e.g. by means of an affinity matrix.

The double chain Factor X analogue thus obtained can subsequently be isolated, purified and stored stably until further use, as described above.

In a particular embodiment, double chain, optionally purified Factor X analogue is brought into contact in vitro with a protease selected from the group of endoproteases, such as kexin/Kex2, furin/PACE, PC1/PC3, PC2, PC4, PACE 4, LPC/PC7, the group of serine proteases, such as Factor XIIa, Factor XIa, Factor Xa, Factor IIa or kallikrein, or a derivative of these proteases, under conditions under which the Factor X analogue is activated to native Factor Xa or a Factor Xa analogue.

According to an embodiment, activation is achieved by a chromatographic step, wherein the protease is immobilized on a carrier. Purified double chain Factor X analogue is passed over a matrix having protease bound thereto, and purified Factor Xa is isolated from the eluate.

According to another embodiment, the components are mixed, and the protease is selectively removed from the mixture.

Of course, also a combination of processing of single chain pro-Factor X analogue to the double chain Factor X analogue form and activation to Factor Xa in one single process is possible. Single chain Factor X analogue or a precursor thereof is directly brought into contact with a dibasic protease, preferably furin or a derivative thereof allowing processing to light and heavy chain and activation to Factor Xa. Factor X analogue having no cleavage site for furin or a derivative thereof in the activation peptide is optionally brought into contact with another protease, different from the first proteases, which allows activation. The proteases can be present in mixture, e.g. of furin and Factor XIa.

Activation can also be effected by a combination of the two steps by means of sequentially arranged and directly interconnected devices, preferably carriers, such as columns, on which the protease(s) is (are) immobilized. At the first carrier Factor X is cleaved to heavy and light chain, and at the second carrier Factor X is activated to Factor Xa by the immobilized protease. The carriers can be coupled by directly connecting the outlet of the first column with the inlet of the second column.

The reaction conditions for the processing reaction(s) and activation can be easily optimized by a person skilled in the art according to the experimental setup and the given basic conditions. For the contact time, the flow rate of the present reactants is of particular importance. Ideally it should be between 0.01 ml/min and 1 ml/min. Further important parameters are temperature, pH value and eluation conditions. After passage, activated Factor Xa can optionally be further purified by selective chromatography. It is particularly advantageous to conduct the process with protease bound to a carrier, because when using a carrier, preferably chromatographic columns, the reaction setup allows for an additional purification step.

According to a further aspect of the preparation of a Factor X analogue, Factor X analogue is isolated as a single chain molecule. Factor X analogue is expressed in a cell which does not support Factor X single chain processing into heavy-light chain. The cell is preferably deficient in a dibasic endoprotease, such as kexin, furin, PACE. In making the invention, it was found that one of the essential proteases responsible for the cleavage of Factor X in light and heavy chain is furin. From such an endoprotease deficient mutant cell, Factor X analogue can be isolated as a single chain molecule. A Factor X analogue thus isolated and optionally purified is subsequently brought into contact with a protease selected from the group of endoproteases, such as kexin/Kex2, furin/PACE, PC1/PC3, PC2, PC4, PACE 4, LPC/PC7, under conditions under which single chain Factor X analogue is cleaved to double chain Factor X form. Factor X analogues of the invention having a modification in the region of the activation peptide allowing cleavage by one of these endoproteases can be optionally activated directly to Factor Xa or Factor Xa analogue by this method by bringing them into contact with the endoprotease.

Factor X analogues according to the invention having a modification in the region of the activation peptide allowing cleavage by a serine protease or kallikrein are brought into contact with a further protease, different from the first, after preparation of double chain Factor X analogue, and are activated to Factor Xa analogue.

According to an aspect of the invention, in the process a preparation containing active Factor Xa or active Factor Xa analogue is obtained by subjecting a Factor X analogue prepared as described above to an activation step and further processing the activated polypeptide to a purified preparation, which is optionally formulated as a pharmaceutical composition.

With the Factor X analogues according to the invention which are activated by a process as described above to Factor Xa, purified Factor Xa or Factor Xa analogue having high stability and structural integrity and being particularly free of inactive Factor X/Xa intermediates is obtained.

The invention is described in more detail by the following Examples, with the invention, however, not being restricted to these particular examples.

Example 1 illustrates the construction and expression of rFactor X; Example 2 illustrates the processing of rFactor X into heavy and light chain by furin; Example 3 illustrates the processing of pro-Factor X by means of immobilized protease; Example 4 illustrates the activity of rFactor X processed in vitro; Example 5 illustrates the expression of rFactor X in furin deficient cells; Example 6 illustrates the construction of rFactor X analogues; Example 7 illustrates the determination of the N-termini of the Factor X processing products; Example 8 illustrates the expression and characterization of the Factor X analogue carrying the furin cleavage site Arg-Arg-Lys-Arg/Ile (SEQ ID NO:75) (rFXRRKR/I); Example 9 illustrates in vitro activation of the rFXRRKR/I protein by r-furin derivatives; Example 10 illustrates the functionality of in vitro activated recombinant FX analogue rFXRRKR/I; Example 11 illustrates in vitro activation of the rFX analogue carrying the cleavage site Asp-Phe-Thr-Arg/Val (SEQ ID NO:76) for Factor XIa.

FIGURES

Figure 2B:
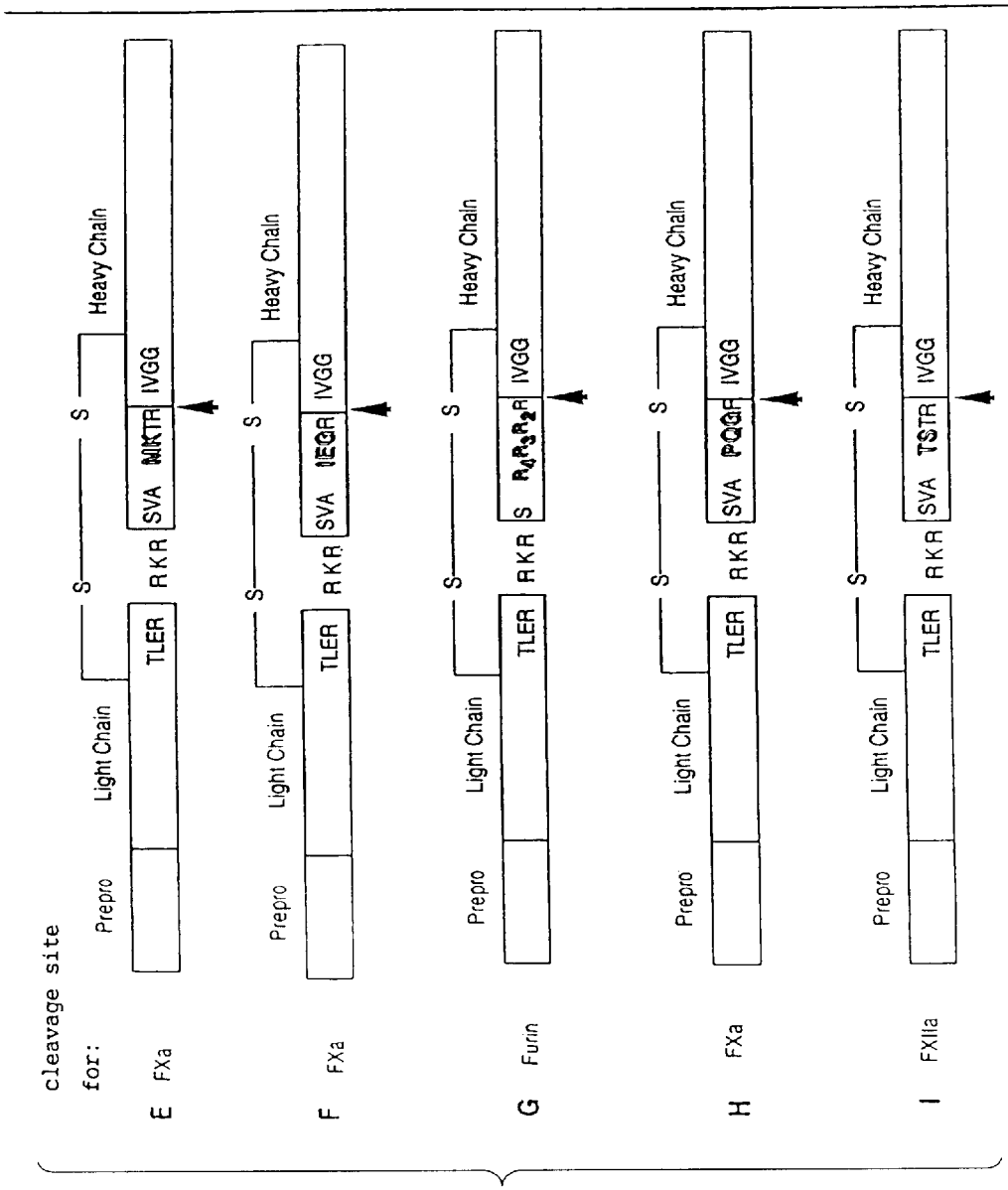
Figure 3:
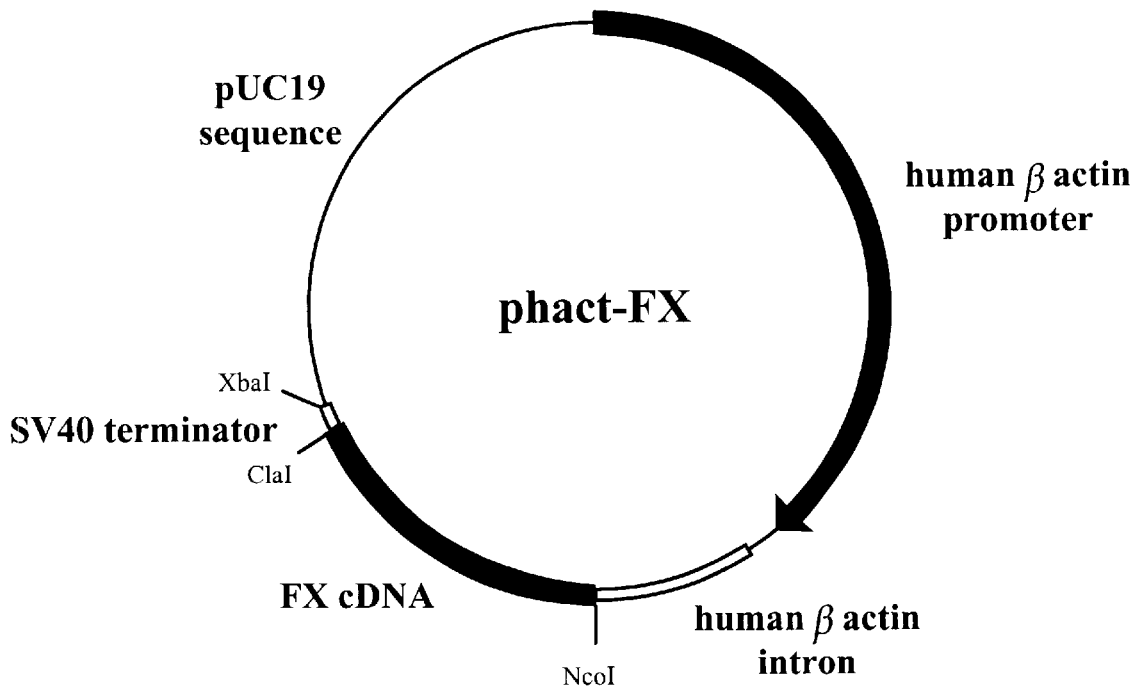
FIG. 3: schematic representation of the expression vector phAct-rFX.
Figure 4:
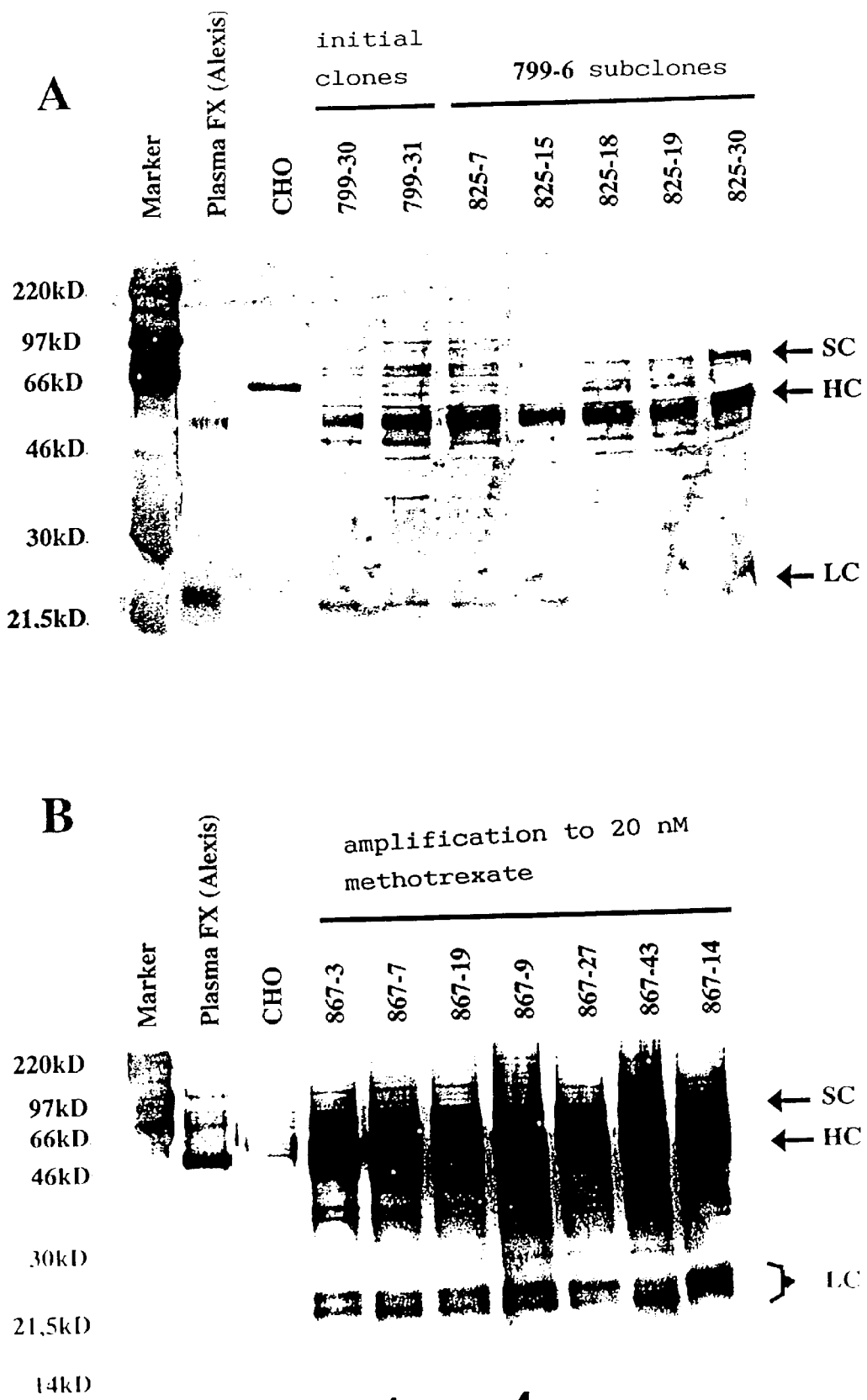
FIGS. 4A and 4B: Western blot analysis of rFactor X expressed in CHO cells before and after amplification.
Figure 6:
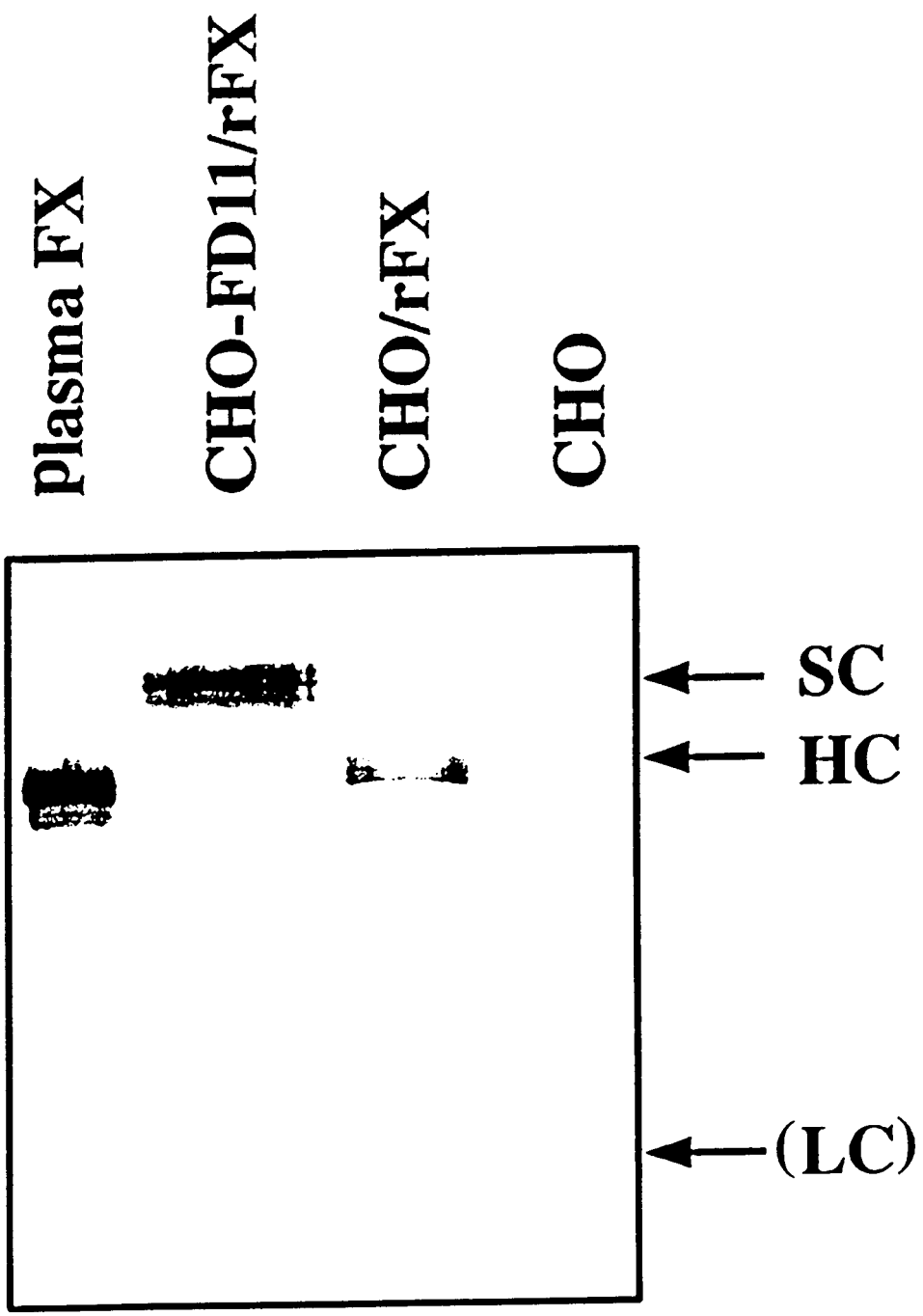
FIG. 6: Western blot analysis of rFactor X molecules expressed in furin containing and furin deficient cells.
Figure 7:
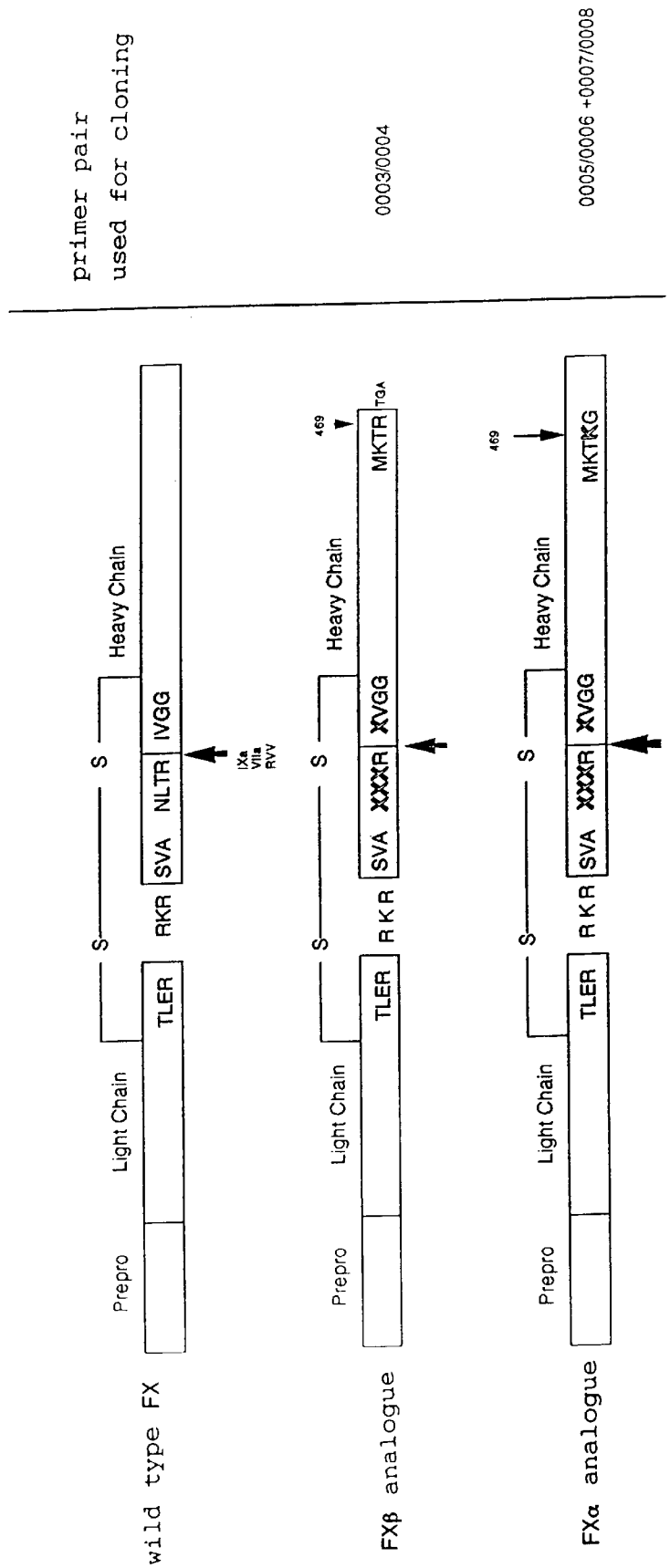
FIG. 7: schematic representation of rFX/rFXa analogue constructs having modified C-termini of the heavy chain (SEQ ID NOS:77, 78 and 96–98).
Figure 9:
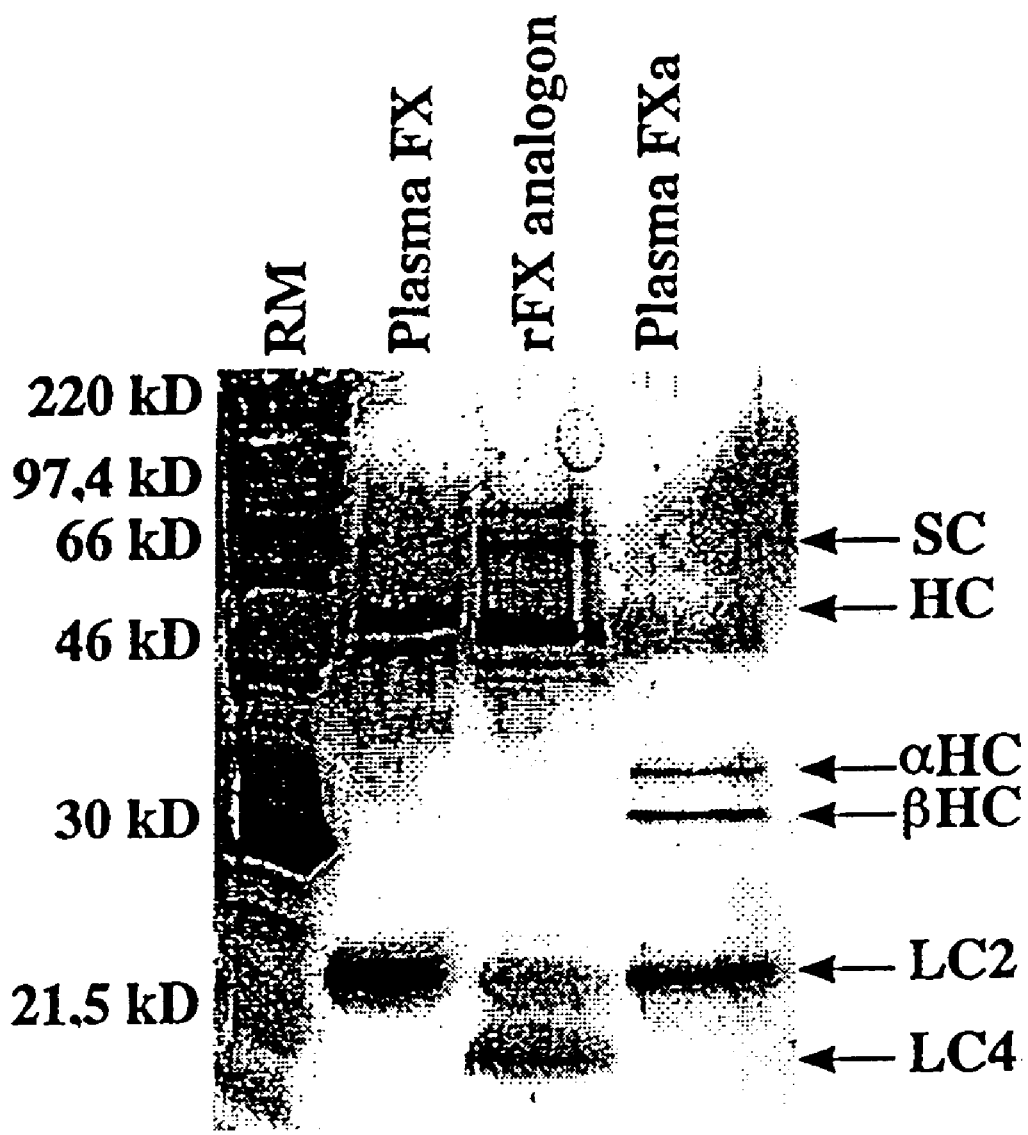
FIG. 9: Western blot analysis of rFactor $FX^{RRKR/I}$ expressed in CHO cells.
Figure 10:
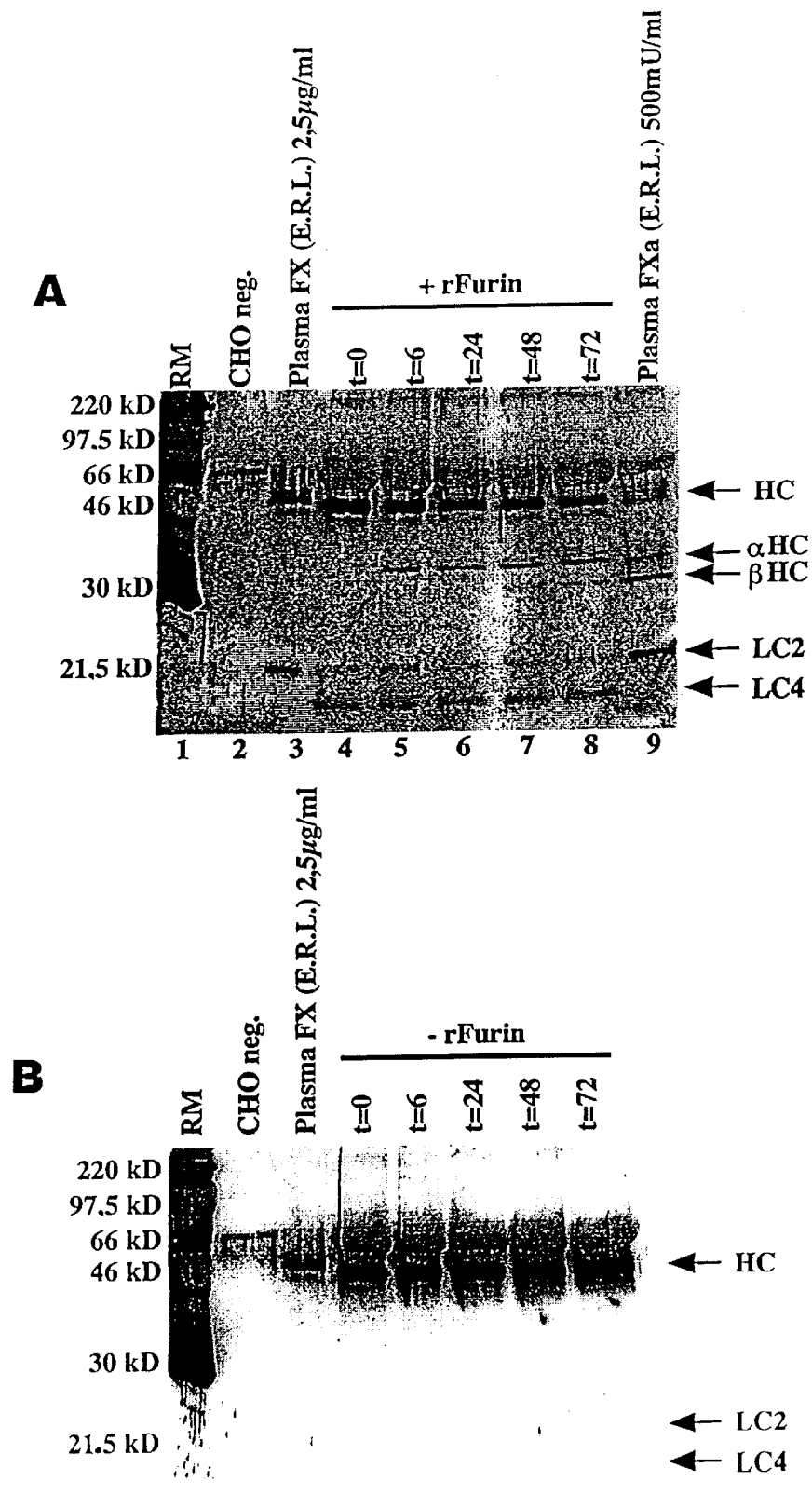
FIGS. 10A and 10B: Western blot analysis of rFactor $FX^{RRKR/I}$ after in vitro activation with furin derivative.
Figure 11:
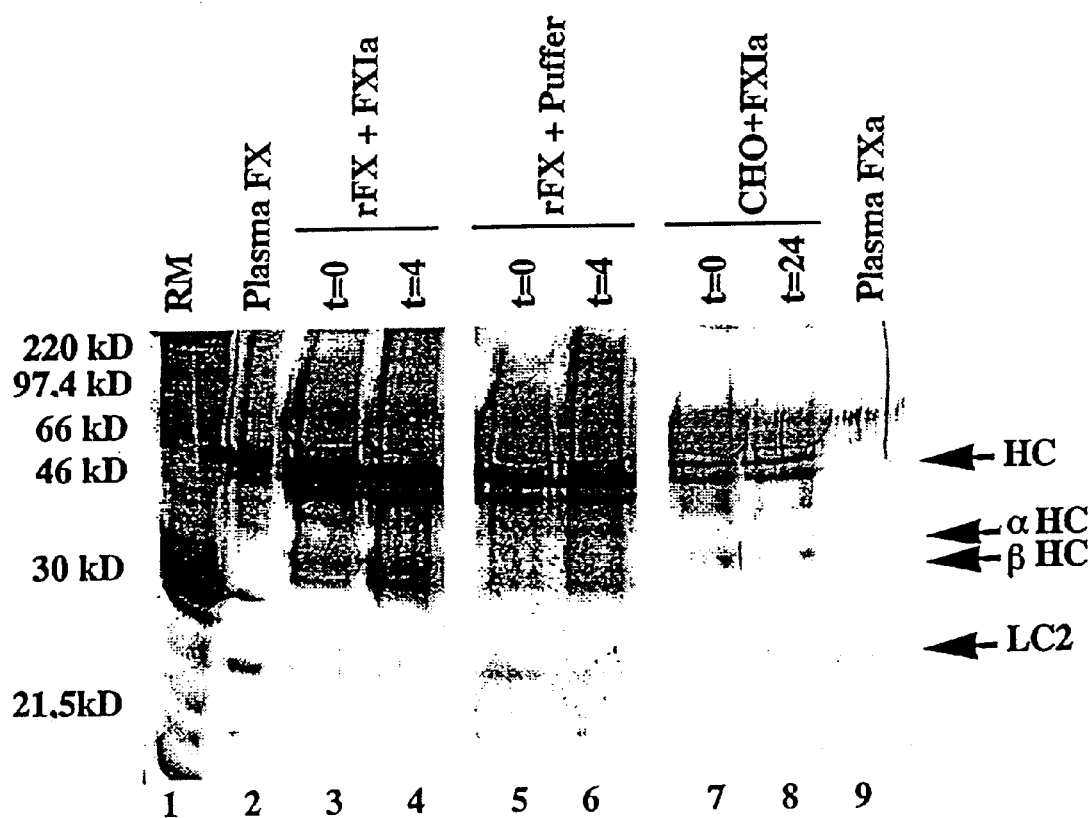
FIG. 11: Western blot analysis of rFactor $FX^{DFTR/V}$ after in vitro activation with furin derivative.

FIG. 1: nucleotide and amino acid sequence of Factor X (SEQ ID NOS:26 and 27)
FIG. 2: schematic representation of the Factor X analogues having modified protease cleavage sites in the region of the activation peptide (SEQ ID NOS:77–95)
FIG. 3: schematic representation of the expression vector phAct-rFX
FIG. 4: Western blot analysis of rFactor X expressed in CHO cells before and after amplification
FIG. 5: Western blot analysis of rFactor X after in vitro cleavage by furin derivatives
FIG. 6: Western blot analysis of rFactor X molecules expressed in furin containing and furin deficient cells
FIG. 7: schematic representation of rFX/rFXa analogue constructs having modified C-termini of the heavy chain (SEQ ID NOS:77, 78 and 96–98)
FIG. 8: schematic representation of the N-termini of rFactor X processing products of furin containing and furin deficient CHO cells prior to and after additional treatment with recombinant furin (SEQ ID NOS:99–104)
FIG. 9: Western blot analysis of rFactor FXRRKR/I expressed in CHO cells
FIG. 10: Western blot analysis of rFactor FXRRKR/I after in vitro activation with furin derivative
FIG. 11: Western blot anaysis of rFactor FXDFTR/V after in vitro activation with furin derivative.

The expression vectors were prepared by means of standard cloning techniques (Maniatis et al., "Molecular Cloning"—A Laboratory<Manual, Cold Spring Harbor Laboratory, Cold Spring Harbor, New York, U.S.A., 1983). The preparation of DNA fragments by means of polymerase chain reaction (PCR) followed general methods (Clackson et al., 1991 m., PCR A practical approach. Ed. McPherson, Quirke, Taylor, pp. 187–214).

EXAMPLE 1

Expression and Processing of Single Chain rFX to rFX Light/heavy Chain a. Construction of the rFX Expression Vector For the preparation of recombinant FX (rFX), the cDNA of FX was isolated from a human liver lambda-cDNA-library as described by Messier et al. (1991, Gene 99:291–294). A DNA fragment was amplified from a positive clone by means of PCR with oligonucleotide #2911 (5'-ATTACTCGAGAAGCTTACCATGGGGCGCCC ACTG-3') (SEQ. ID No.1) as 5'-primer and oligonucleotide #2912 (5'-ATTACAATTGCTGCAGGGATCCAC-3') (SEQ. ID. No. 2) as 3'-primer. This DNA fragment contains the 1,467 kB FX encoding sequence and 39 bp of the 3' non-translated region, flanked by a XhoI cleavage site at the 5'- end and a MfeI cleavage site at the 3'- end. In addition, the sequence ACC was incorporated in front of the ATG of the FX by means of the primer #2911 resulting in an optimal Kozak translation initiation sequence. Subsequently, this PCR product was cloned as XhoI/MfeI fragment in the expression vector phAct cleaved with SalI and EcoRI. The resulting expression plasmide was designated as phAct-rFX (FIG. 3). The expression vector phAct comprises the human beta-actin promotor 78 bp 5' UTR and the intron, a multiple cloning cleavage site, and the SV40 polyadenylation site.

b. Expression of rFX in CHO Cells

In order to establish a stable rFX expressing cell line, dhfr deficient CHO cells were co-transfected with the expression plasmide phAct-rFX and the selection marker plasmide pSV-dhfr. For all further expression and function analyses, the cells were incubated with serum free selection medium in the presence of 10 µg/ml vitamin K for 24 hours. The expression of rFX in the resulting cell clones was detected by means of the amount of antigen (ELISA, Asserachrom, Boehringer Mannheim), and the recombinant protein was characterized with SDS-PAGE (FIGS. 4A and B). As can be seen in the Western blot (FIG. 4A), in the initial clones and subclones thereof there is the recombinant FX protein present in the form of a light chain (LC) of 22 kD and a heavy chain (HC) of approximately 50 kD, which are identical in size with the plasma Factor X chains. In addition, a protein band is visible at 75 kD, which corresponds to the single chain (SC) molecule and the presence of which in FX transfected CHO cells (Wolf et al., J. Biol. Chem. 266:13726–13730, 1991) and in human plasma (Fair et al., Blood 64:194–204, 1984) has been described. For the preparation of highly expressing clones, the initial clones were amplified with increasing amounts of methotrexate and subsequently subcloned to stabilization. Expression could be increased from about 200–500 ng/10 E6 cells and 1 µg/ml, respectively, to 78 µg/10 E6 cells and 120 µg/ml, respectively, per 24 hours. Western blot analysis of these highly expressing cell clone supernatants (FIGS. 4B and 5A, lane 2) shows increased, quantities of the single chain rFX molecule and the presence of additional forms of the light chain. Besides the 22 kD form of the light chain, which corresponds to the plasmatic form (fully carboxylated and without propeptide) there are three additional light chain variants of about 21 kD, 22.5 kD, and 20 kD present. By means of N-terminal sequencing of the recombinant material, the heterogeneity of the light chain in these clones was attributed to be incomplete cleavage of the propeptide (here: about 50% of the rFX material) and hypocarboxylation (here: about 50% of the rFX). The 21 kD protein is a hypocarboxylated, propeptide containing form, and the 20 kD protein is a hypocarboxylated, propeptide-free form of the light chain, while the 22.5 kD band represents the fully carboxylated, but pro-peptide containing LC form.

EXAMPLE 2

Processing of Single Chain rFX in rFX Light/heavy Chain by Rfurin Derivatives

Due to the similarity of the cleavage sites of Factor X propeptide/N-terminus of the light chain (RVTR↓A); SEQ ID NO:105) and between light/heavy chain (RRKR↓S); SEQ ID NO:106) to the furin consensus recognition sequence (RXK/RR↓X); SEQ ID NO:107), it seems possible to improve in vitro processing of single chain as well as propeptide containing rFX molecules by rfurin derivatives. In the literature, proteases are suspected for the two processing steps, which, however, are not furin (Rehemtulla et al., 1992, Blood 79:2349–2355; Wallin et al., 1994, Thromb. Res. 1994:395–403).

Cell culture supernatants of CHO-rFX and CHO-rfurin ATM6xHis (patent application EP 0 775 750 A2) as well as CHO-rFX and untransfected CHO (as negative control) were mixed at a ratio of 1:1 and incubated at 37° C. Aliquots of the reaction mixtures were tested for processed rFX before incubation (t=0) and after various incubation periods (t=2, 4, 6 hours) by Western blot analysis (FIG. 5). The rFX was detected in the cell culture supernatants by means of an anti-human FX antiserum (FIG. 5A) and a monoclonal antibody specific for the light chain of FX (FIG. 5B).

As opposed to the CHO-rFX/CHO mixture, the CHO-rFX/CHO-rfurin shows almost complete processing already after 2 hours of incubation at 37° C. (FIG. 5A, lane 7; FIG. 5B, lane 8). Single chain rFX is largely converted into the light and heavy chain form. In the area of the light chain, only the processed propeptide-free forms of 22 kD (carboxylated form) and 20 kD (hypo-carboxylated form) were found at a ratio of about, 50:50. By optimizing cell culture conditions, this ratio can be improved in favor of the carboxylated form. Correct cleavage of the pro-sequence between Arg-1 and Ala+1 and homogeneity of the N-terminus of the light chain were determined by N-terminal sequencing. In the control experiment, wherein CHO-rFX was mixed with CHO-supernatants, no change in the rFX band pattern is visible even after 6 hours of incubation (FIG. 5A, lane 5; FIG. 5B, lane 6). This proves that rfurin in the supernatant of CHO cells is biologically active and can process the propeptide as well as the heavy/light chain of rFX.

EXAMPLE 3

Processing of Factor X by Means of Chelate-tentacle Gel Immobilized Rfurin

In order to investigate whether a substrate can be cleaved by column-bound rfurin derivative, a study was conducted as to whether Fractogel EMD® tentacle gel (Merck) can be used in an experimental setup alternatively to $Ni^{2+}$-NTA agarose, as a column matrix. As the metal ions are farther apart from the actual column matrix than in $Ni^{2+}$-NTA agarose, sterical access of the substrate to the bound rfurin derivative could be improved. In the present setup, pro-Factor X was processed by tentacle gel bound rfurin derivative: Fractogel EMD® tentacle gel was loaded with $Ni^{2+}$ ions according to the producer's instructions and equilibrated with fresh serum-free cell culture medium. Subsequently, the column was loaded with serum-free CHO-rfurin derivative supernatant. Washing steps were carried out by serum-free cell culture medium containing increasing imidazole concentrations up to 40 mM. Then pro-Factor X was passed over the column as serum-free CHO supernatant. Processing of pro-Factor X to double chain Factor X was detected in the effluent of the column by means of Western blot analysis with specific Factor X antiserum.

EXAMPLE 4

Activity of Recombinant Factor X Processed in vitro

Recombinant Factor X precursor was incubated with and without rfurin at 4° C. At different times, samples were taken and frozen at −20° C. After the incubation was completed (after 4 days), all samples were tested for FX activity using the FX Coatest Kit (Chromogenix). 50 µl of each supernatant were mixed with 50 µl FX deficient human plasma, and rFX was activated with snake venom (RVV) to rFXa in the presence of $CaCl_2$ according to the producer's instructions; rFXa then hydrolyzes the chromogenic substrate (S-2337) and leads to the release of yellow-coloured paranitroaniline. As the amount of rFXa and the intensity of the colour are proportionate to each other, the amount of rFX/ml cell culture supernatant which is activated to rFXa can be determined by means of a calibration line interpolated from values of a plasma dilution series. Using these results and the known amount of rFX antigen (ELISA data), the proportion of rFactor X activated to Factor Xa can be calculated in %. The results are presented in Table 1.

In order to exclude nonspecific, proteolytic activity in CHO and CHO-rfurin supernatants, the mixture of these two cell culture supernatants was tested, too.

Even after 4 days, CHO-rFX incubated with CHO supernatants (without rfurin) as control displayed no substantial change in rFXa activity, which was about 800 mU/ml and corresponded to 55%–61% of functional rFX due to experimental variations. When, in comparison, CHO-rFX was incubated with CHO-rfurin, rFX activity increased steadily during incubation, rising from 61% (T=0) to 86% (Table 1). This proves that in vitro processing of CHO-rFX from highly expressing clones using rfurin derivative substantially improves the proportion of rFX that can be activated to functional rFXa.

TABLE 1

|  | incubation (days) | activity (mU) | amount of antigen (µg/ml) | functional portion of rFX (%) |
|---|---|---|---|---|
| CHO-rFX + | 0 | 814 | 14 | 58 |
| CHO | 1 | 847 | 14 | 61 |
|  | 2 | 835 | 14 | 60 |
|  | 3 | 790 | 14 | 56 |
|  | 4 | 763 | 14 | 55 |
| CHO-rFX + | 0 | 853 | 14 | 61 |
| CHO-rFurin | 1 | 1018 | 14 | 73 |
|  | 2 | 1099 | 14 | 79 |
|  | 3 | 1135 | 14 | 81 |
|  | 4 | 1198 | 14 | 86 |
| CHO + CHO-rFurin |  | 0 |  |  |
| Plasma FX 500 mU |  | 585 |  |  |

EXAMPLE 5

Expression of Recombinant Factor X in Furin Deficient Cells

As show in the previous examples, in the case of Factor X precursor protein, furin mediates propeptide cleavage as well as cleavage of the single chain to light/heavy chain vitro. This suggests that these cleavages are also performed endogenously in the cell by ubiquitous furin with varying efficiency depending on the amount of expressed rFactor X. This in turn leads to the production of a mixture of heterogenous rFactor X forms.

One way to prepare a form of rFactor X molecules which is as homogeneous as possible and also stable is to prevent cleavage of rFactor X by endogenous proteases, particularly furin, and thus to produce functionally inactive rFactor X precursor (which can be transformed into their functionally active forms later by means of downstream processing, ideally directly before use). This method will be particularly useful in the preparation of FX analogues containing a furin cleavage site instead of the original activation site. In these constructs, such a recombinant rFX mutant could be activated in vivo by endogeneous furin and lead to the secretion of activated, more instable rFX forms. Degradation of these forms, e.g. under cell culture conditions of high cell lysis by CHO proteases during storage of the cell culture supernantants or the purifying process, or by autoproteolysis, could result in inactive degradation products (Wolf et al., 1991).

This aim can, for instance, be achieved by supplementing the cell culture medium with agents which can reduce or prevent intracellular furin activity.

Another way is to use cells which are furin deficient a priori (Möhring et al., 1983, Infect. Immun. 41:998–1009; Ohnishi et al., 1994, J. Virol. 68:4075–4079; Gordon et al., 1995, Infect. Immun. 63:82–87).

For this purpose, a furin deficient CHO cell clone FD11 (Gordon et al., 1995, Infect. Immun. 63:82–87) was co-transfected with 20 μg phAct-FX and 1 μg pUCSV-neo (containing the neomycin resistance gene in the pUC vector under control of the SV40 promotor). In order to obtain stable clones, the medium was supplemented with 0,8 μg G418/ml. Comparing secreted rFactor X molecules in serum free supernatants of a furin containing and a furin deficient CHO clone, Western blot shows that rFactor X precursor is not processed in the furin deficient cells and only single chain Factor X precursor is present (FIG. 6); in contrast, rFactor X is completely processed by "normal" cells at modest expression, but is processed only to a very limited extent with higher expression in spite of endogenous furin. Due to the low rFX expression level of the cell clone used for this analysis, the light chain of rFactor X is not visible in this blot.

EXAMPLE 6

Preparation of Factor X Analogues 6.1. Construction of Expression Plasmids for the Preparation of Factor X Analogue.

For the preparation of recombinant rFactor X analogue, the cleavage site Asn-Leu-Thr-Arg/Ile (amino acid 231 to 235) serving for the activation of Factor X to Factor Xa was replaced by a cleavage site specific for a different protease, such as furin, FXIa, FXa, FXIIa, FII or kallikrein. The expression plasmids for these Factor X analogues are all derived from plasmid phAct-Fx (described in Example 1).

In order to simplify cloning of Factor X expression plasmids, the HindIII-NaeI DNA fragments from the phAct-FX expression plasmid, which comprises the Factor X encoding region from position +1 to +1116, was inserted into the HindIII/SmaI restriction cleavage site of plasmid pUC19. The resulting plasmid was designated as pUC/FX.

Thus, the Factor X sequence of nucleotide at position 508 to 705 (amino acids 160 to 235) could easily be removed from pUC/FX plasmid and replaced by various mutated Factor X DNA fragments. These DNA fragments are identical with the deleted wild type Factor X sequence except for positions 691 to 705 (amino acids 231 to 235) which code for new cleavage sites.

The wild type Factor X sequence was removed from the pUC/FX plasmid via Bsp120I and BstXI restriction digests. The 3'-overhang of the BstXI site was additionally removed with mung bean nuclease (Biolab).

The mutated Factor X DNA fragments were prepared by means of PCR. The 5'-primer is identical for all clonings and contains the Factor X sequence of position 496 to 516. The 3'-primers contain a sequence complementary to Factor X (position 676 to 690) and a non-complementary 5'-end carrying the sequences for a new cleavage site and a restriction cleavage site. The amplified PCR product was subsequently digested by the appropriate restriction enzyme (s) and cloned in the prepared pUC/Fk vector (see above).

Subsequently, the mutated Factor X DNA fragments were re-cloned via HindIII-AgeI from the pUC/FX plasmids into the phAct-FX vector. The final constructs are schematically represented in FIGS. 2A and 2B. Factor X wild type is given as a reference construct. The amino acids are given in the form of a one-letter code, the mutated positions are additionally shaded.

In order to prepare the Asp-Phe-Thr-Arg/Val (SEQ ID NO:76) FXIa cleavage site, the oligonucleotide #1001 (5'-CCC ACA GGG CCC TAC CCC TGT-3') (SEQ ID NO:3) was used as a 5'-primer, and the oligonucleotide #1002 (5'-ACCA-GTT AAC CCT GGT GAA GTC GTT GTC GCC CCT CTC-3') (SEQ ID NO:4) was used as a 3'-primer. Thus, the amino acids Asn, Leu and Ile at positions 231, 232, and 235 of the Factor X sequence were substituted by Asp, Phe and Val. The PCR fragment was trimmed by means of Bst120I and HpaI (FIG. 2A, Panel A). The PCR fragment was trimmed by means of Bst120I and HpaI (FIG. 2A).

In order to prepare an Arg/Ser FIIa cleavage site, the oligonucleotide #1001 (5'-CCC ACA GGG CCC TAC CCC TGT-3') (SEQ ID NO:3) was used as a 5'-primer, and the oligonucleotide #1003 (5'-ACCA TCG CGA CCT GGT CAG GTT GTT GTC3') (SEQ ID NO:5) was used as a 3'-primer. Thus, the amino acid Ile at position 235 was mutated into Ser. The PCR fragment was trimmed by means of Bsp120I and NruI (FIG. 2A, Panel B).

In order to prepare an Ile-Lys-Pro-Arg/Ile (SEQ ID NO:109) FXIIa cleavage site, the oligonucleotide #1001 (5'-CCC ACA GGG CCC TAC CCC TGT-3') (SEQ ID NO:3) was used as a 5'-primer, and the oligonucleotide #1004 (5'-ACC AGA ATC GAT TCT GGG TTT GAT GTT GTC GCC CCT CTC-3') (SEQ ID NO:6) was used a s a 3' primer. Thus, the amino acids Asn, Leu and Thr at positions 231, 232 and 233 of the FX sequence were mutated into Ile, Lys and Pro. The PCR fragment was trimmed with Bst120I and partially with XmnI (FIG. 2A, Panel C).

In order to prepare Ser-Met-Thr-Arg/Ile (SEQ ID NO:110) kallikrein cleavage site, the oligonucleotide #1001 (5'-CCC ACA GGG CCC TAC CCC TGT-3') (SEQ ID NO:3) was used as 5'-primer, and the oligonucleotide #1005 (5'-ACC AGA ATC GAT TCT GGT CAT GCT GTT GTC GCC CCT CTC-3') (SEQ ID NO:7) was used as a 3' primer. Thus, the amino acids Asn, Leu at positions 231, 232 of the Factor X sequence were mutated into Ser, Met. The PCR fragment was digested with Bst120I and partially with XmnI (FIG. 2B, Panel D).

In order to prepare a Pro-Gln-Gly-Arg/Ile (SEQ ID NO:111) FXa cleavage site, the oligonucleotide #1001 (5'-CCC ACA GGG CCC TAC CCC TGT-3') (SEQ ID NO:3) was used as a 5'-primer, and the oligonucleotide #1016 (5'-ACC AGA ATC GAT TCT TCC TTG GGG GTT GTC GCC CCT CTC-3') (SEQ. ID. No. 8) was used as a 3' primer. Thus, the amino acids Asn, Leu and Thr at positions 231, 232 and 233 of the FX protein were mutated to Pro, Gln and Gly. The PCR fragment was trimmed with Bst120I and partially with XmnI (FIG. 2B, Panel H).

In order to prepare a Met-Lys-Thr-Arg/Ile (SEQ ID NO:112) FXa cleavage site, the oligonucleotide #1001 (5'-CCC ACA GGG CCC TAC CCC TGT-3') (SEQ ID NO:3) was used as a 5'-primer, and the oligonucleotide #1014 (5'-ACC AGA ATC GAT TCT CGT TTT CAT GTT GTC GCC CCT CTC-3') (SEQ ID NO:9) was used as a 3' primer. Thus, the amino acids Asn, Leu at positions 231, 232 of the FX protein were mutated to Met, Lys. The PCR fragment was trimmed with Bst120I and partially with XmnI (FIG. 2B, Panel E).

In order to prepare an Ile-Glu-Gly-Arg/Ile (SEQ ID NO:113) FXa cleavage site, the oligonucleotide #1001 (5'-CCC ACA GGG CCC TAC CCC TGT-3') (SEQ ID NO:3) was used as a 5'-primer, and the oligonucleotide #1015 (5'-ACC AGA ATC GAT TCT TCC CTC GAT GTT GTC GCC CCT CTC-3') (SEQ ID NO:10) was used as a 3' primer. Thus, the amino acids Asn, Leu and Thr at positions 231 to 233 of the FX protein were mutated to Ile, Glu, Gly. The PCR fragment was trimmed with Bst120I and partially with XmnI (FIG. 2B, Panel F).

In order to prepare an Arg-Arg-Lys-Arg/Ile (SEQ ID NO:114) furin cleavage site, the oligonucleotide #1001 (5'-CCC ACA GGG CCC TAC CCC TGT-3') (SEQ ID NO:3) was used as a 5'-primer, and the oligonucleotide #1006 (5'-ACC AGA ATC GAT TCT TTT CCT CCT GTT GTC GCC CCT CTC-3') (SEQ ID NO:11) was used as a 3' primer. Thus, the amino acids Asn, Leu and Thr at positions 231 to 233 were mutated to Arg, Arg and Lys. The PCR fragment was trimmed with Bsp120I and partially with XmnI (FIG. 2B, Panel G).

In order to prepare an Arg-Val-Arg-Arg/Ile (SEQ ID NO:115) furin cleavage site, the oligonucleotide #1001 (5'-CCC ACA GGG CCC TAC CCC TGT-3') (SEQ ID NO:3) was used as a 5'-primer, and the oligonucleotide #1007 (5'-ACC AGA ATC GAT TCT CCT CAC CCT GTT GTC GCC CCT CTC-3') (SEQ ID NO:12) was used as a 3' primer. Thus, the amino acids Asn, Leu and Thr at positions 231 to 233 were mutated to Arg, Val and Arg. The PCR fragment was trimmed with Bsp120I and partially with XmnI (FIG. 2B, Panel G).

In order to prepare an Arg-Arg-Arg-Arg/Ile (SEQ ID NO:116) furin cleavage site, the oligonucleotide #1001 (5'-CCC ACA GGG CCC TAC CCC TGT-3') (SEQ ID NO:3) was used as a 5'-primer, and the oligonucleotide #1008 (5'-ACC AGA ATC GAT TCT CCT CCT CCT CGTT GTC GCC CCT CTC-3') (SEQ ID NO:13) was used as a 3' primer. Thus, the amino acids Asn, Leu and Thr at positions 231 to 233 were mutated to Arg, Arg and Arg. The PCR fragment was trimmed with Bsp120I and partially with XmnI (FIG. 2B, Panel G).

In order to prepare an Arg-Pro-Lys-Arg/Ile (SEQ ID NO:117) furin cleavage site, the oligonucleotide #1001 (5'-CCC ACA GGG CCC TAC CCC TGT-3') (SEQ ID NO:3) was used as a 5'-primer, and the oligonucleotide #1009 (5'-ACC AGA ATC GAT TCT TTT GGG CCT GTT GTC GCC CCT CTC-3') (SEQ ID NO: 14) was used as a 3' primer. Thus, the amino acids Asn, Leu and Thr at positions 231 to 233 were mutated to Arg, Pro and Lys. The PCR fragment was trimmed with Bsp120I and partially with XmnI (FIG. 2B, Panel G).

In order to prepare an Ile-Arg-Lys-Arg/Ile (SEQ ID NO:118) furin cleavage site, the oligonucleotide #1001 (5'-CCC ACA GGG CCC TAC CCC TGT-3') (SEQ ID NO:3) was used as a 5'-primer, and the oligonucleotide #1010 (5'-ACC AGA ATC GAT TCT TTT CCT GAT GTT GTC GCC CCT CTC-3') (SEQ ID NO:15) was used as a 3' primer. Thus, the amino acids Asn, Leu and Thr at positions 231 to 233 were mutated to Ile, Arg and Lys. The PCR fragment was trimmed with Bsp120I and partially with XmnI (FIG. 2B, Panel G).

In order to prepare an Arg-Ser-Lys-Arg/Ile (SEQ ID NO:119) furin cleavage site, the oligonucleotide #1001 (5'-CCC ACA GGG CCC TAC CCC TGT-3') (SEQ ID NO:3) was used as a 5'-primer, and the oligonucleotide #1011 (5'-ACC AGA ATC GAT TCT TTT GCT CCT GTT GTC GCC CCT CTC-3') (SEQ ID NO:16) was used as a 3' primer. Thus, the amino acids Asn, Leu and Thr at positions 231 to 233 were mutated to Arg, Ser and Lys. The PCR fragment was trimmed with Bsp120I and partially with XmnI (FIG. 2B, Panel G).

In order to prepare an Arg-Val-Thr-Arg/Ile (SEQ ID NO:120) furin cleavage site, the oligonucleotide #1001 (5'-CCC ACA GGG CCC TAC CCC TGT-3') (SEQ ID NO:3) was used as a 5'-primer, and the oligonucleotide #1012 (5'-ACC AGA ATC GAT TCT GGT CAC CCT GTT GTC GCC CCT CTC-3') (SEQ ID NO:17) was used as a 3' primer. Thus, the amino acids Asn, Leu at positions 231, 232 were mutated to Arg, Val. The PCR fragment was trimmed with Bsp120I and partially with XmnI (FIG. 2B, Panel G).

In order to prepare an Arg-Leu-Lys-Arg/Ile (SEQ ID NO:121) furin cleavage site, the oligonucleotide #1001 (5'-CCC ACA GGG CCC TAC CCC TGT-3') (SEQ ID NO:3) was used as a 5'-primer, and the oligonucleotide #1013 (5'-ACC AGA ATC GAT TCT TTT GAG CCT GTT GTC GCC CCT CTC-3') (SEQ ID NO:18) was used as a 3' primer. Thus, the amino acids Asn and Thr at positions 231 and 233 were mutated to Arg and Lys. The PCR fragment was trimmed with Bsp120I and partially with XmnI (FIG. 2B, Panel G).

In order to prepare an Thr-Ser-Thr-Arg/Ile (SEQ ID NO:122) FXIIa cleavage site, the oligonucleotide #1001 (5'-CCC ACA GGG CCC TAC CCC TGT-3') (SEQ ID NO:3) was used as a 5'-primer, and the oligonucleotide #1017 (5'-ACC AGA ATC GAT TCT CGT GCT CGT GTT GTC GCC CCT CTC-3') (SEQ ID NO:19) was used as a 3' primer. Thus, the amino acids Asn, Leu at positions 231, 232 of the FX protein were mutated to Ile, Lys. The PCR fragment was trimmed with Bst120I and partially with XmnI (FIG. 2B, Panel I).

6.2. Construction of Expression Plasmids for the Preparation of FXβ Analogue

Figure 8:
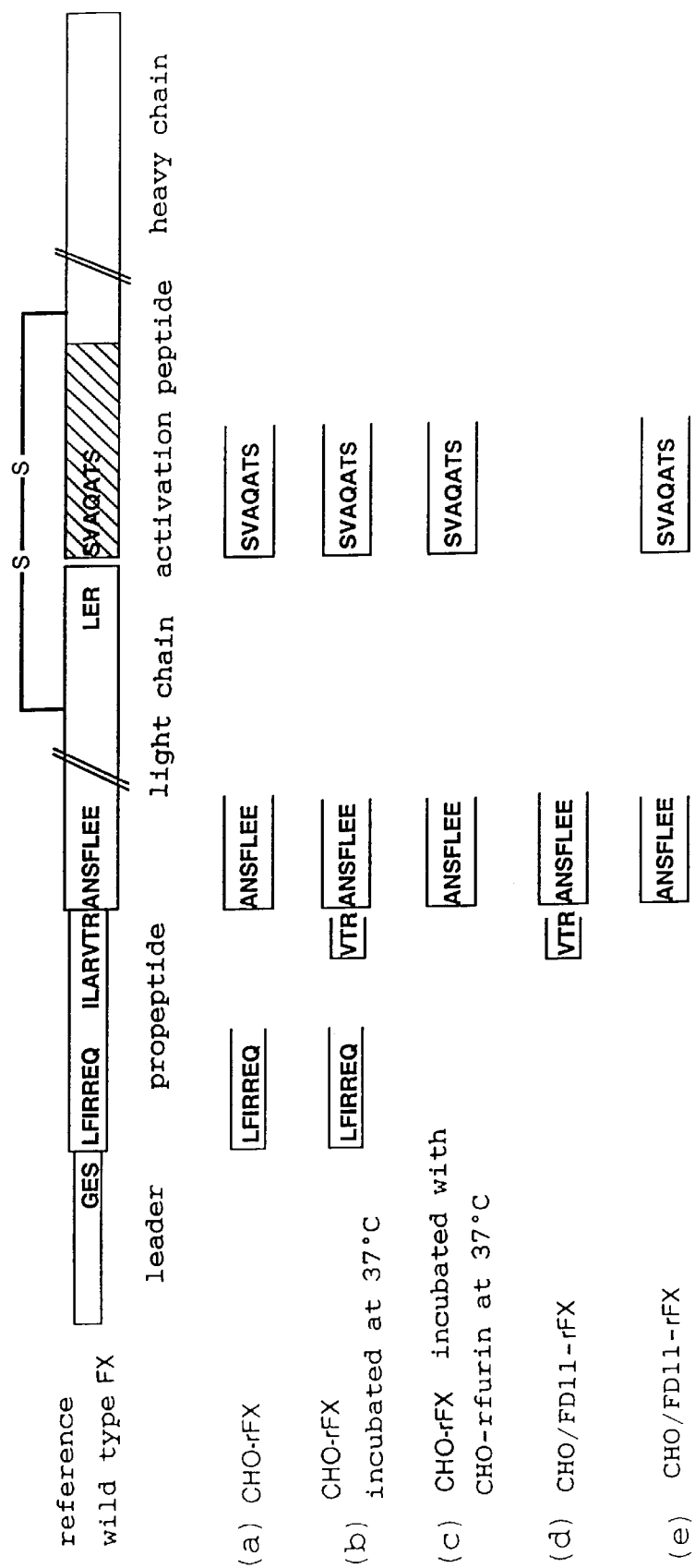
FIG. 8: schematic representation of the N-termini of rFactor X processing products of furin containing and furin deficient CHO cells prior to and after additional treatment with recombinant furin (SEQ ID NOS:99–104).

These constructs were derived from the Factor X analogue constructs described above by introducing a TGA stop codon at position 470. The amino acids from position 457 to the stop codon on cDNA level were removed by SpeI and partial gstEII digestion and replaced by the oligonucleotide pair #0003 (5'-GTC ACC GCC TTC CTC AAG TGG-ATC GAC AGG TCC ATG AAA ACC AGG TGA A-3') (SEQ. ID. No. 20) and #0004 (5'-CTA GTT CAC CTG GTT TTC ATG GAC CTG TCG ATC CAC TTG AGG AAG GCG-3') (SEQ. ID. No. 21). FIG. 7 is a schematic representation of the Factor Xβ analogue constructs. In order to simplify the figure, all Factor Xβ analogues are represented as a general construct wherein the variable amino acids in the cleavage site regions are shown as a shaded "X".

6.3. Construction of Expression Plasmids for the Preparation of FXa Analogue

By activating Factor X by removal of the 4.5 kDa activation peptide at the N-terminal end of the heavy chain, the Factor Xaα form is generated. This form is subsequently converted into the FXaβ form by autoproteolytic activity and cleavage in the C-terminus of the heavy chain between Arg469 and Gly470. For the preparation of Factor X expression plasmids leading to the production of Factor X, which will be present after activation exclusively in the FXaα form with intact β-peptide, the amino acid Arg469 was mutated to Lys so that this region of the heavy chain can not be cleaved any more.

For this purpose, the C-terminal amino acid sequence of Factor X from position 1363 to the stop signal was removed by partial BstEII-SpeI digestion and replaced by two ligated oligonucleotide pairs. Oligonucleotide #0005 (5'-GTC ACC GCC TTC CTC AAG TGG ATC GAC AGG TCC ATG AAA ACC AAG GGC TTG CCC AAG-3') (SEQ. ID. No. 22) and oligonucleotide #0006 (5'-TTG GCC TTG GGC AAG CCC TTG GTT TTC ATG GAC CTG TCG ATC CAC TTG AGG AAG GCG-3') (SEQ. ID. No. 23) were ligated with oligonucleotide #0007 (5'-GCC AAG AGC CAT GCC CCG GAG GTC ATA ACG TCC TCT CCA TTA AAG TGA GAT CCC A-3') (SEQ. ID. No. 24) and oligonucleotide #0008 (5'-CTA GTG GGA TCT CAC TTT AAT GGA GAG GAC GTT ATG ACC TCC GGG GCA TGG CTC-3') (SEQ. ID. No. 25). The mutation of amino acid Arg469 is introduced by the oligonucleotide pair #0005-#0006. FIG. 7 shows a schematic representation of the FX analogues.

EXAMPLE 7

Determination of the N-termini of Factor X and Processing Products with and Without r-furin Recombinant Factor X was expressed in CHO cells with endogenous furin, as described in Example 1, and in furin deficient cells, as described in Example 5. rFactor X was isolated from cell culture supernatant of highly expressing CHO-rFX clones, which was a) untreated, b) incubated at 37° C. for an additional 12 hours, c) incubated with CHO-rfurin supernatant at 37° C. for a period of 12 hours, as well as from cell culture supernatant of CHO-FD11-rFX clones which was d) untreated, and e) incubated with CHO-rfurin supernatant at 37° C. for a period of 12 hours. The N-terminal amino acids of Factor X and the processing products of the individual reaction mixtures a) to e) were determined by Edman analysis. FIG. 8 shows a schematic representation of the results.

rFactor X from highly expressing CHO cells is present in the form of the mature heavy and light chains as well as in the single chain form, partly still containing propeptide. After incubation of these cell culture supernatants for 12 hours at 37° C. (b), additional faulty N-termini of the rFX light chain having 3 additional amino acids Val38-Thr39-Arg40 are formed, as already described by Wolf et al. (1991, J. Bio. Chem. 266:13726–13730). These cryptic ends are also found when sequencing rFX material from untreated CHO-FD11 cells (d). This observation shows that the formation of these faulty N-termini can be prevented by optimized conditions, i.e. cell culture conditions, storage and purifying processes in order to minimize rFX proteolysis by CHO proteases.

Contrary to the purified material from CHO cells (a and b), rFX from non-amplified, furin deficient cells (d) is only present in the form of unprocessed single chain precursors. N-terminal sequences corresponding to the propeptide portion are not found, either. This shows that single chain rFX precursor is not processed any more to light/heavy chain in furin deficient CHO cells (d), which suggests a central role of the endoprotease furin in this processing step in vivo. In addition, it shows that rFX molecules containing propeptide are also processed in furin deficient CHO cells, i.e. that furin does not play an essential role in this processing step in vivo. After incubation of rFX from CHO cells (c) and CHO-FD11 cells (e) in the presence of furin, only light and heavy chains having correct N-termini are found. This proves that the single chain FX precursors as well as the rFX molecules containing propeptide are converted to homogeneous, mature Factor X by in vitro processing. Thus, Factor X processed in the presence of furin exhibits exceptional structural integrity and homogeneity.

EXAMPLE 8

Expression and Characterization of the FX Analogue Having the Furin Cleavage Site Arg-Arg-Lys-Arg/Ile (rFX$^{RRKR/I}$)

The FX expression plasmid having the cleavage site Arg-Arg-Lys-Arg/Ile (SEQ ID NO:75) (see Example 6.1, FIG. 2B, Panel G) and the selection plasmid pSV/dhfr were co-transfected in CHO cells, as described in Example 1, in order to prepare recombinant rFX$^{RRKR/I}$ protein. Western blot analysis of the cell culture supernatants (FIG. 9) shows that the recombinant protein is mainly present in the double chain form. As compared to plasma FX, the heavy chain runs at 46 kD instead of 50 kD, which may be ascribed to changes in the glycosylation of the recombinant protein. In addition, small amounts of single chain precursor (SC) and the LC4 isoform of the light chain become apparent, as already observed when expressing wild type rFX (Example 1.b). These molecular forms of the rFX analogue suggest that processing of the single chain FX precursor by endogenous proteases as well as γ-caboxylation of the light chain are limited. Although the cleavage site introduced into the FX analogue represents a furin consensus sequence, no protein bands are visible which would correspond to the activated forms of the protein (35 kD, 31 kD). The structure of the cleavage site region or the neighboring amino acid sequence seem to represent a suboptimal configuration for the processing of the modified activation site by furin in vivo.

EXAMPLE 9

In vitro Activation of the rFX$^{RRKR/I}$ Protein by r-furin Derivatives

The ability of the recombinant FX analogue to be activated to the α (35 kD) and β (31 kD) FXa forms by r-furin in vitro was tested as described in Example 2 by mixing experiments. The tests differed, however, in that the purified r-furin derivatives rfurinΔCys-spacer-10×His, described in patent application EP 0 775 750-A2, in 10 mM hepes pH 7.0, 150 mM NaCl, 2 mM CaCl$_2$ and 0.2% BSA were used instead of CHO-rfurin supernatants. In the control experiment without r-furin, CHO-rFX analogue supernatant was mixed with the buffer 10 mM hepes pH 7.0, 150 mM CaCl, 2 mM CaCl$_2$ and 0.2% BSA at a ratio of 1:1. Aliquots of the reaction mixtures before and after an incubation period of 6, 24, 48 and 72 hours (t=0, 6, 24, 48, 72) at 37° C. were tested for rFX activation by means of Western blot (FIGS. 10A and 10B). While the band pattern of rFX$^{RRKR/I}$ remained unchanged in the absence of the r-furin derivative even after 72 hours of incubation (FIG. 10B), in the presence of r-furin a 35 kD heavy protein band corresponding to the α-form of plasmatic FX (FIG. 10A, lane 9) appears already after 6 hours (FIG. 10A, lane 5). In the course of incubation, this a-form accumulates and after 72 hours of incubation (FIG. 10A, lane 8), about 50% of the starting material (HC) have been converted to the activated form. The additional 31 kD heavy protein band, which appears after 24 hours (FIG. 10A, lane 6) and corresponds to the β-form of the activated plasma FX (FIG. 10A, lane 9), shows that the α-form generated from recombinant FX analogue has autoproteolytic activity and is therefore functional.

These results prove that the heterologous activation cleavage site Arg-Arg-Lys-Arg/Ile (SEQ ID NO:75) in the rFX analogue is specifically recognized and correctly cleaved by r-furin derivatives in vitro and is thus adapted to activate the rFX analogue to the α-and β-FXa molecules.

EXAMPLE 10

Functionality of the Recombinant FX Analogue rFX$^{RRKR/I}$ Activated in vitro

Aliquots of the mixing experiment of Example 9 were tested for FXa activity by means of a chromogen test. The aliquots were mixed with the chromogen substrate S2337 (600 μM) in 50 mM Tris pH 7.3, 150 mM NaCl, 0.1% BSA. After an incubation period of 3 minutes at 37° C., the reaction was stopped by means of 20% acetic acid, and then OD was measured at 405 nm. The amount of recombinant FXa activity in the reaction mixutres was determined by comparison with a calibration curve, prepared by means of purified, RVV-activated plasma FXa. The results of this analysis, the amounts of antigen used (ELISA data), and the specific activity calculated therefrom are presented in Table 2.

In order to exclude undesired amidolytic activities in the r-furin solution and the CHO cell culture supernatant, the mixture of supernatants of non-transfected CHO cells with purified r-furin derivative was tested for FXa activity, too (CHO+rfurin). In this mixture; exactly as in the rFX analogue/buffer mixture (rFX$^{RRKR/I}$+buffer), no FXa activity was detected even after 72 hours of incubation. In contrast, in the case of the rFX$^{RRKR/I}$/rfurin reaction, an rFXa activity of 56 mU was detectable already after 6 hours of incubation, which increased constantly in the course of incubation and amounted to 133 mU after 72 hours. Although at this point, according to Western blot, only about half of the rFX analogue had been reacted to the activated α- and β-forms (FIG. 10A, lane 8), the rFX analogue material activated in vitro showed a far higher specific activity of 190 mU/μg than the plasma FX completely activated with RVV (153 mU/μg). The measured increases in activity correspond to the emergence of the α- and β-forms in Western blot (FIG. 10A, lanes 5–8).

This proves that heterologuous protease cleavage sites can be incorporated into FX, which are recognized and cleaved by the respective protease, and that high quality rFXa (or, optionally, rFXa analogues having FXa activity) in functional form can be prepared by recombinant technology.

TABLE 2

| | incubation (hours) | activity (mU/ml) | amount of antigen (μg/ml) | specific activity mU/μg |
|---|---|---|---|---|
| rFX$^{RRKR/I}$ + buffer | 0 | <25 | 0.7 | 0 |
| | 6 | <25 | 0.7 | 0 |
| | 24 | <25 | 0.7 | 0 |
| | 48 | <25 | 0.7 | 0 |
| | 72 | <25 | 0.7 | 0 |
| rFX$^{RRKR/I}$ + rfurin | 0 | <25 | 0.7 | 0 |
| | 6 | 56 | 0.7 | 80 |
| | 24 | 101 | 0.7 | 144 |
| | 48 | 124 | 0.7 | 177 |
| | 72 | 133 | 0.7 | 190 |
| CHO + rfurin | 0 | <25 | 0 | |
| | 6 | <25 | 0 | |
| | 24 | <25 | 0 | |
| | 48 | <25 | 0 | |
| | 72 | <25 | 0 | |
| RVV activated plasma FX | | 614 | 4 | 153 |

A FX analogue construct was prepared by mutagenesis. of the FX activation sequence to a FXIa cleavage site. Subsequently, stable CHO cell clones were established which express these molecules. CHO cell culture supernatant containing rFX$^{DFTR/V}$ was mixed with purified plasma FXIa (100 μg/ml) in the presence of 10 mM Tris pH 7.3, 150 mM NaCl, 8 mM $CaCl_2$, PCPS and 0.1% BSA, and was incubated at 37° C. for various periods of time. As negative control, the cell culture supernatant was incubated only with buffer containing BSA. The rFX$^{DFTR/V}$ protein and the resulting activation products were analyzed by Western blot analysis (FIG. 11). As can be seen in the mixture without FXIa before incubation (t=0), the recombinant protein (FIG. 11, lane 5) is almost identical to the plasma FX (lane 2) in the double chain form, the only difference being that the heavy chain (HC) has a molecular weight of slightly less than 50 kD, as was already observed in the case of rFX$^{RRKR}$ in Example 8. During incubation of this mixture at 37° C. (FIG. 11, lane 6), no significant change in the band pattern appears. In the CHO-rFX analogue/FXIa mixture, protein bands of 35 kD and 31 kD rapidly appear after the addition of purified FXIa, but prior to the actual incubation of the cell sulture supernatant (FIG. 11, lane 3). These bands correspond by their size to the plasma α- and β-forms of the heavy chain (FIG. 11, lane 9). These two forms increase considerably after 4 hours of incubation with FXIa (FIG. 11, lane 4).

This shows that a FX analogue carrying the heterologous protease cleavage site for a proteolytic enzyme active in the coagulation cascade can also by processed successfully by the latter.

In addition, functional activity of the resulting rFXaα analogue is successfully demonstrated by the occurrence of the rFXaβ band, the result of autoproteolytic activity of rFXaα analogue.

What is claimed is:

1. A Factor X analogue comprising a Factor X amino acid sequence wherein there is an amino acid modification in a region between Gly228 and Arg 234 of SEQ ID NO:27, said modification resulting in a processing site for a protease other than trypsin, Factor IXa, FactorVIIa and Russell's viper venom in said region.

2. A Factor X analogue as set forth in claim 1, wherein said modification is a substitution of at least one amino acid within the region.

3. A Factor X analogue as set forth in claim 2, wherein said modification is an exchange of at least two amino acids between Gly228 and Arg234 of SEQ ID NO:27.

4. A Factor X analogue as set forth in claim 3, wherein said Factor X amino acid sequence has a further modification, said further modification being an exchange of Ile235 of SEQ ID NO:27.

5. A Factor X analogue as set forth in claim 1, said Factor X analogue comprising a Factor X amino acid sequence wherein amino acids Gly228 to Arg 234 and residue 235 of SEQ ID NO:27 have the sequence Gly228-R6-R5-R4-R3-R2-Arg 234-R1, wherein, a) R1 is an amino acid selected from the group consisting of Ile, Val, Ser, Thr and Ala, b) R2 is an amino acid selected from the group consisting of Pro, Gly, Lys and Arg, c) R3 is an amino acid selected from the group consisting of Phe, Lys, Met, Gln, Glu, Ser, Val, Arg and Pro, d) R4 is an amino acid selected from the group consisting of Asp, Ile, Ser, Met, Pro, Thr, Arg and Lys, e) R5 is an amino acid selected from the group consisting of Asn, Lys, Ser, Glu, Ala, Gln, His and Arg, and f) R6 is an amino acid selected from the group consisting of Asp, Phe, Thr, Arg, Leu and Ser.

6. A Factor X analogue as set forth in claim 1, wherein said modification results in a processing site for a protease selected from the group consisting of an endoprotease, a serine protease, and a derivative of these proteases.

7. A Factor X analogue as set forth in claim 6, wherein said endoprotease is selected from the group consisting of kexin/Kex2, furin/PACE, PC1/PC3, PC2, PC4, PACE 4, and LPC/PC7, and said serine protease is selected from the group consisting of Factor IIa, Factor XIIa, Factor XIa, Factor Xa and kallikrein.

8. A Factor X analogue as set forth in claim 1, wherein said Factor X amino acid sequence has a further modification said further modification occurring at Lys370 and/or within a segment extending from Arg469 to Ser476 of SEQ ID NO:27.

9. A Factor X analogue as set forth in claim 8, wherein said further modification is a substitution located at the β-peptide cleavage site located between Arg469 and Gly470 of SEQ ID NO:27.

10. A Factor X analogue as set forth in claim 8, wherein said further modification is selected from a mutation, a deletion and an insertion between amino acid positions Arg469 and Ser476 of SEQ ID NO:27.

11. A Factor X analogue as set forth in claim 8, wherein said further modification prevents the β-peptide extending from Gly470 to Lys488 of SEQ ID NO:27 from being cleaved off.

12. A Factor X analogue as set forth in claim 1, wherein said Factor X amino acid sequence has a further modification which is a deletion of Factor X β-peptide which extends from Gly470 to Lys488 of SEQ ID NO:27.

13. A Factor X analogue as set forth in claim 1, further comprising a translation stop signal in a C-terminal region of the Factor X amino acid sequence, said C-terminal region extending from Arg469 to Lys488 of SEQ ID NO:27.

14. A Factor X analogue as set forth in claim 13, wherein the translation stop signal is at the position of amino acid 470 of SEQ ID NO:27.

15. A Factor X analogue as set forth in claim 1, wherein said modification allows for an activation of said Factor X analogue to at least one of native Factor Xa and Factor Xa analogue in vitro.

16. A Factor X analogue as set forth in claim 15, wherein said modification allows for an activation by a protease selected from the group consisting of an endoprotease, a serine proteases, and a derivative of said proteases.

17. A Factor X analogue as set forth in claim 16, wherein said endoprotease is selected from the group consisting of kexin/Kex2, furin/PACE, PC1/PC3, PC2, PC4, PACE 4, and LPC/PC7, and said serin protease is selected from the group consisting of Factor IIa, Factor XIIa, Factor XIa, Factor Xa and kallikrein.

18. A Factor X analogue as set forth in claim 1, wherein said modification allows for an activation of said Factor X analogue to at least one of native Factor Xa and Factor Xa analogue in vivo.

19. A Factor X analogue as set forth in claim 18, wherein said protease is a serine protease.

20. A Factor X analogue as set forth in claim 19, wherein said serine protease is selected from the group consisting of Factor XIIa, Factor XIa, Factor IIa, Factor Xa and kallikrein.

21. A Factor X analogue as set forth in claim 1, wherein said Factor X analogue is a Factor X analogue having an intact β-peptide, said β-peptide extending from Gly470 to Lys488 of SEQ ID NO:27.

22. A Factor X analogue as set forth in claim 1, wherein said Factor X analogue is a C-terminally shortened Factor X analogue that lacks a segment from the C-terminal region, said C-terminal region extending from Arg469 to Lys488 of SEQ ID NO:27.

23. A Factor X analogue as set forth in claim 1, wherein said Factor X analogue is a single chain molecule.

24. A preparation comprising a purified Factor X analogue or a precursor protein of said purified Factor X analogue, said Factor X analogue comprising a Factor X amino acid sequence wherein there is at least one amino acid modification in a region between Gly228 and Arg234 of SEQ ID NO:27, said modification resulting in a processing site for a protease other than trypsin, Factor IXa, FactorVIIa and Russell's viper venom in said region.

25. A preparation as set forth in claim 24, wherein said protease is selected from the group consisting of a dibasic endoprotease and a serine protease.

26. A preparation as set forth in claim 25, wherein said dibasic endoprotease is selected from the group consisting of kexin/Kex2, furin/PACE, PC1/PC3, PC2, PC4, PACE 4 and LPC/PC7, and said serine protease is selected from the group consisting of Factor IIa, Factor XIIa, Factor XIa and Factor Xa and kallikrein.

27. A preparation as set forth in claim 24, wherein said Factor X analogue is a Factor Xa analogue.

28. A preparation as set forth in claim 24, wherein said Factor X analogue is a Factor X analogue that lacks a segment from the C-terminal region, said C-terminal region extending from Arg469 to Lys488 of SEQ ID NO:27.

29. A preparation as set forth in claim 24, wherein said Factor X analogue is present as a single-chain molecule.

30. A preparation as set forth in claim 29, wherein said single-chain Factor X analogue is present in an enzymatically inactive form, and has a purity of at least 80%.

31. A preparation as set forth in claim 30, wherein said purity is at least 90%.

32. A preparation as set forth in claim 30, wherein said purity is at least 95%.

33. A preparation as set forth in claim 24, wherein said Factor X analogue is present as a double-chain molecule.

34. A preparation as set forth in claim 24, wherein said modification in said Factor X analogue allows for an activation of Factor X analogue to native Factor Xa or to Factor Xa analogue in vitro.

35. A preparation as set forth in claim 24, wherein said preparation is formulated as a pharmaceutical preparation.

36. A preparation as set forth in claim 24, wherein said preparation is provided in a device in combination with a protease selected from the group consisting of an endoprotease, a serine protease and a derivative of said proteases.

37. A preparation as set forth in claim 36, wherein said endoprotease is selected from the group consisting of kexin/Kex2, furin/PACE, PC1/PC3, PC2, PC4, PACE 4, and LPC/PC7, and said serine protease is selected from the group consisting of Factor XIIa, Factor XIa, Factor Xa, Factor IIa and kallikrein.

38. A preparation as set forth in claim 36, wherein said device is an application device adapted for administration of the preparation to a patient.

39. A preparation as set forth in claim 36, wherein said Factor X analogue and said protease are contained in separate spaces of said device.

40. A preparation as set forth in claim 24, wherein said processing site allows for an activation of the Factor X analogue to native Factor Xa or to Factor Xa analogue in vivo.

41. A preparation as set forth in claim 24, further comprising a physiologically acceptable carrier, said preparation being provided in storage stable form.

42. A preparation as set forth in claim 24, further comprising a component selected from the group consisting of a blood factor and an activated form of a blood factor.

43. A preparation as set forth in claim 42, wherein said component comprises at least one component having Factor VIII bypass activity.

44. A preparation as set forth in claim 42, wherein said preparation is formulated as a pharmaceutical composition.

45. A preparation as set forth in claim 44, wherein said preparation is provided as a multiple compound preparation.

46. A preparation comprising a Factor Xa analogue free from inactive intermediates formed during processing or autoproteolysis of Factor X or Factor X analogue and obtained by activation of said Factor X analogue, said Factor X analogue comprising a Factor X amino acid sequence wherein there is at least one amino acid modification in a region between Gly228 and Arg234 of SEQ ID NO:27, said modification resulting in a processing site for a protease other than trypsin, Factor IXa, FactorVIIa and Russell's viper venom in said region.

47. A process for producing a preparation comprising purified recombinant Factor X analogue in single-chain or double-chain form, said method comprising
  a) producing a recombinant Factor X analogue, wherein said Factor X analogue comprises a Factor X amino acid sequence wherein there is at least one amino acid modification in a region between Gly228 and Arg 234 of SEQ ID NO:27, said modification resulting in a processing site for a protease other than trypsin, Factor IXa, FactorVIIa and Russell's viper venom in said region; and
  b) purifying said Factor X analogue to obtain said preparation.

48. A process as set forth in claim 47, wherein
  producing comprises
    (i) providing a vector containing a nucleic acid encoding the Factor X analogue;
    (ii) transforming a cell with said vector; and
    (iii) expressing said Factor X analogue in said cell; and
  purifying comprises
    (i) isolating said Factor X analogue from said cell; and
    (ii) purifying said isolated Factor X analogue by a chromatographic method.

49. A process as set forth in claim 48, further comprising incubating said expressed Factor X analogue with a protease.

50. A process as set forth in claim 49, wherein said protease is immobilized.

51. A process as set forth in claim 48, wherein said cell does not express a protease that can cleave Factor X or said Factor X analogue in single chain form into a light and a heavy chain.

52. A process as set forth in claim 51, wherein said Factor X analogue is purified as a single-chain molecule.

53. A process as set forth in claim 52, further comprising contacting said single-chain Factor X analogue, with a protease selected from the group of endoproteases consisting of kexin/Kex2, Furin/PACE, PC1/PC3, PC2, PC4, PACE 4, and LPC/PC7 or a derivative of these proteases under conditions under which said single-chain Factor X analogue is cleaved to a double-chain-form.

54. A process as set forth in claim 53, further comprising activating said single-chain Factor X analogue directly to Factor Xa or to a Factor Xa analogue.

55. A process as set forth in claim 54, wherein said protease is immobilized and said single-chain X analogue is activated by contacting said single-chain Factor analogue with said immobilized protease.

56. A process as set forth in claim 53, further comprising contacting said double-chain Factor X analogue with a further protease different from said protease, thereby activating said double-chain Factor X analogue to a Factor Xa analogue or to native Factor Xa.

57. A process as set forth in claim 48, wherein said cell does not express an endoprotease that can cleave Factor X or said Factor X analogue in single chain form into a light and a heavy chain.

58. A process as set forth in claim 57, wherein said endoprotease is selected from the group consisting of kexin, furin, PACE and a derivative of these endoproteases.

59. A process as set forth in claim 47, wherein said Factor X analogue is purified as a double-chain molecule.

60. A process as set forth in claim 59, further comprising contacting said double-chain Factor X analogue with a protease selected from the group consisting of an endoprotease, a serine protease and a derivative of these proteases, under condition in which said Factor X analogue is cleaved to native Factor Xa or to a Factor Xa analogue.

61. A process as set forth in claim 60, wherein said endoprotease is selected from the group consisting of kexin/Kex2, furin/PACE, PC1/PC3, PC2, PC4, PACE 4, and LPC/PC7, and said serine protease is selected from the group consisting of Factor IIa, Factor XIIa, Factor XIa, Factor Xa and kallikrein.

62. A process as set forth in claim 60, wherein said cell is deficient of a protease that can cleave Factor X or said Factor X analogue in single chain form into a light and a heavy chain.

63. A process of producing a preparation comprising Factor Xa or Factor Xa analogue, said method comprising subjecting a Factor X analogue to an activation step, wherein said Factor X analogue comprises a Factor X amino acid sequence wherein there is a modification in a region between Gly228 and Arg 234 of SEQ ID NO:27, said modification resulting in a processing site for a protease other than trypsin, Factor IXa, FactorVIIa and Russell's viper venom in said region.

64. A process as set forth in claim 63, wherein purified Factor Xa analogue or native Factor Xa free from inactive intermediates formed during processing or autoproteolysis of Factor X or Factor X analogue is obtained by activation of the Factor X analogue.

\* \* \* \* \*